US008053633B1

(12) United States Patent
Hildebrand et al.

(10) Patent No.: US 8,053,633 B1
(45) Date of Patent: Nov. 8, 2011

(54) FUNGAL DESATURASES AND RELATED METHODS

(75) Inventors: David Hildebrand, Lexington, KY (US); Suryadevara Rao, Lexington, KY (US); John Thoguru, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 246 days.

(21) Appl. No.: 12/346,234

(22) Filed: Dec. 30, 2008

(51) Int. Cl.
*A01H 5/00* (2006.01)
*C12N 15/82* (2006.01)
*C07H 21/04* (2006.01)

(52) U.S. Cl. ..... 800/281; 800/298; 435/419; 435/320.1; 536/23.2

(58) Field of Classification Search .................. None
See application file for complete search history.

(56) References Cited

U.S. PATENT DOCUMENTS 6,495,738 B1 * 12/2002 Folkerts et al. ............... 800/281

OTHER PUBLICATIONS

Broun et al, Science 282:1315-1317, Nov. 13, 1998.*
Van de Loo et al, PNAS USA 92:6743-6747, Jul. 1995.*
Doerks et al, TIG 14(6): 248-250, Jun. 1998.*
Brenner, S.E. TIG 15(4):132-133, Apr. 1999.*
Bork et al, TIG 12(10):425-427, Oct. 1996.*
Mitchell, A., Martin CE. 1995. A novel cytochrome b5-like domain is linked to the carboxyl terminus of the *Saccharomyces cerevisiae* delta-9 fatty acid desaturase. J Biol Chem. 270: 29766-29772.
Petrini. G.; Altabe, SG, Uttaro, AD. 2004. *Trypanosoma brucei* oleate desaturase may use a cytochrome b5-like domain in another desaturase as an electron donor. Eur. J. Biochem. 271: 1079-1086.
Watts, J., Browse, J. 2000. A Palmitoyl-CoA-Specific 9 Fatty Acid Desaturase from *Caenorhabditis elegans*. Biophys Biochem Res Commun. 272: 263-269.
Wongwathanarat, P., L. V. Michaelson, A. T. Carter, C. M. Lazarus, G. Griffiths, A. K. Stobart, D. B. Archer, and D. A. MacKenzie. 1999. Two fatty acid Delta 9-desaturase genes, ole1 and ole2, from *Mortierella alpina* complement the yeast ole1 mutation. Microbiology-(UK) 145: 2939-2946.
Prasad, M., Joshi VC 1979. Purification and properties of hen liver microsomal terminal enzyme involved in stearoyl coenzyme A desaturation and its quantitation in neonatal chicks. J Biol Chem. 254: 6362-6363.
Strittmatter, P., Spatz L, Corcoran D, Rogers MJ, Sellow B, Redline R.. 1974. Purification and properties of rat liver microsomal stearyl coenzyme A desaturase. Proc Natl Acad Sci, 71: 4565-4569.
Choi JY, S. J., Hwang SY, Martin CE. 1996. Regulatory elements that control transcription activation and unsaturated fatty acid-mediated repression of the *Saccharomyces cerevisiae* OLE1 gene. J Biol Chem. 271: 3581-3589.
Gonzalez, C., Martin CE. 1996. Fatty acid-responsive control of mRNA stability. Unsaturated fatty acid-induced degradation of the *Saccharomyces* OLE1 transcript. J Biol Chem, 271: 25801-25809.
Anamnart, S., Tomita T, Fukui F, Fujimori K, Harashima S, Yamada Y, Oshima Y., 1997. The P-OLE1 gene of *Pichia angusta* encodes a delta 9-fatty acid desaturase and complements the ole1 mutation of *Saccharomyces cerevisiae*. Gene. 184: 299-306.
Kajiwara, S. 2002. Molecular cloning and characterization of the Delta9 fatty acid desaturase gene and its promoter region from *Saccharomyces kluyveri*. FEMS Yeast Res 2: 333-339.
Sakai, H., Kajiwara, S. 2003 A stearoyl-CoA-specific Delta 9 fatty acid desaturase from the basidiomycete *Lentinula edodes*. Biosci Biotechnol Biochem. 67: 2431-2437.
Reddy, M. S. S., R. D. Dinkins, C.T. Redmond, S.A. Ghabrial, and G.B. Collins. 2001. Expression of Bean pod mottle virus (BPMV) coat protein precursor results in resistance to (BPMV) in transgenic soybeans, Phytapathology, 91: 831-838.
Gietz, R. D., R. H. Schiestl, A. R. Willems, R. A. Woods, and K. S. 1995. Studies on the Transformation of Intact Yeast Cells by the LiAciSS-DNA/PEG Procedure. Yeast. 11: 355-360.
Stukey, J., McDonough, VM , Martin,CE. 1990. The OLE1 gene of *Saccharomyces cerevisiae* encodes the delta 9 fatty acid desaturase and can be functionally replaced by the rat stearoyl-CoA desaturase gene. J. Biol. Chem. 265: 20144-20149.
Mihara, K. 1990, Structure and Regulation of Rat Liver Microsomal Stearoyl-CoA Desaturase Gene. J. Biochem. (Tokyo) 108: 1022-1029.
Kaestner, K. H., Ntambi, J. M., Kelly, T. J., Jr., and Lane, M. D. 1989. Differentiation-induced gene expression in 3T3-L1 preadipocytes. A second differentially expressed gene encoding stearoyl-CoA desaturase, J. Biol. Chem. 264: 14755-11476.
Miyazaki, M., Jacobson, M. J., Man, W. C., Cohen, P., Asilmaz, E., Friedman, J. M., and Ntambi, J. M. . 2003. Identification and characterization of murine SCD4, a novel heart-specific stearoyl-CoA desaturase isoform regulated by leptin and dietary factors. J. Biol. Chem 278: 33904-33911.
Fukuchi-Mizutani, M., Tasaka, Y., Tanaka, Y., Ashikari, T., Kusumi, T. and Murata, N., 1998. Characterization of 9 acyl-lipid desaturase homologues from *Arabidopsis thaliana*. Plant Cell Physiol. 39: 247-253.
Hui, E., Wang PC and Lo SJ. 1998. Strategies for cloning unknown cellular flanking DNA sequences from foreign integrants. Cell Mol Life Sci. 54: 1403-1411.

(Continued)

*Primary Examiner* — Elizabeth McElwain
(74) *Attorney, Agent, or Firm* — Stites & Harbison PLLC; Terry L. Wright

(57) ABSTRACT

The presently-disclosed subject matter provides isolated nucleic acid and amino acid sequences encoding mushroom desaturase polypeptides that are active with both palmitic and stearic acid, as well as vectors and transgenic plant cells comprising nucleic acids of the presently-disclosed subject matter. The presently-disclosed subject matter further provides methods of producing monounsaturated fatty acids, such as palmitoleic acid (16:1), and monounsaturated fatty acids prepared by the methods disclosed herein.

27 Claims, 11 Drawing Sheets

OTHER PUBLICATIONS

Forster, C., Arthur, E, Cresp, S, Hobbs, SL., Mullineaux, P, and Casey, R. 1994. Isolation of a pea (*Pisum sativum*) seed lipoxygenase promoter by inverse polymerase chain reaction and characterization of its expression in transgenic tobacco. Plant Mol Biol. 26: 235-248.

Martin, C., Oh CS, Kandasamy P, Chellapa R, Vemula M. 2002. Yeast desaturases. Biochem Soc Trans. 30: 1080-1082.

Man , W., Miyazaki ,M, Chu ,K, Ntambi, JM 2006. Membrane Topology of Mouse Stearoyl-CoA Desaturase. J. Biol. Chem. 281: 1251-1260.

Dimou, D.M., Georgala, A., Komaitis, M., Aggelis, G. 2002. Mycelial fatty acid composition of *Pleurotus spp*. and its application in the intrageneric differentiation. Mycological Research 106: 925-929.

Shanklin, J., Cahoon, E.B. 1998. Desaturation and Related Modifications of Fatty Acids. Annu. Rev. Plant Physiol. Plant Mol. Biol. 49: 611-641.

Cahoon, E.B., Shanklin, J, Ohlrogge J.B. 1992. Expression of a coriander desaturase results in petroselinic acid production in transgenic tobacco. Proc. Natl. Acad. Sci. USA 89: 11184-11188.

Cahoon, E.B., Ohlrogge, J.B. (1994) 104, 827-844. 1994. Metabolic Evidence for the Involvement of a [delta]4-Palmitoyl-Acyl Carrier Protein Desaturase in Petroselinic Acid Synthesis in Coriander Endosperm and Transgenic Tobacco Cells. Plant Physiol. 104: 827-844.

Schultz, DJ, Cahoon, EB, Shanklin, J, Craig, R, Cox-Foster, DL, Mumma, RO, and J. I. Medford. 1996. Expression of a delta 9 14:0-acyl carrier protein fatty acid desaturase gene is necessary for the production of omega 5 anacardic acids found in pest-resistant geranium (*Pelargonium xhortorum*). Proc. Natl. Acad. Sci. USA 93: 8771-8775.

Mekhedov, S., O. M. de Ilarduya, and J. Ohlrogge. 2000. Toward a Functional Catalog of the Plant Genome. A Survey of Genes for Lipid Biosynthesis. Plant Physiol. 122: 389-402.

Marillia, E. F., E. M. Giblin, P. S. Covello, and D. C. Taylor. 2002. A desaturase-like protein from white spruce is a Delta(9) desaturase. FEBS Letters 526: 49-52.

Cahoon, E., Shanklin, J. 2000. Substrate-dependent mutant complementation to select fatty acid deseturase variants for metabolic engineering of plant seed oils. Proc Natl Acad Sci U S A 97: 12350-12355.

Heilmann, I., S. Mekhedov, B. King, J. Browse, and J Shanklin. 2004. Identification of the *Arabidopsis* Palmitoyl-Monogalactosyldiacylglycerol (Delta)7-Desaturase Gene FAD5, and Effects of Plastidial Retargeting of *Arabidopsis* Desaturases on the fad5 Mutant Phenotype. Plant Physiol, 136: 4237-4245.

Fox, B. G., Shanklin, J., Somerville, C. , Munck,E. 1993. Stearoyl-Acyl Carrier Protein 9 Desaturase from *Ricinus communis* is a Diiron-Oxo Protein. Proc. Natl. Acad. Sci. U S A 90: 2486-2490.

Shanklin, S., Whittle, E, Fox, BG. 1994. Eight Histidine Residues Are Catalytically Essential in a Membrane-Associated Iron Enzyme, Stearoyl-CoA Desaturase, and Are Conserved in Alkane Hydroxylase and Xylene Monooxygenase. Biochemistry. 33: 12787-12794.

Thoguru JVSR, Rao SS, Hildebrand DF. "Cloning, characterization, and application of an oyster mushroom (*Pleurotus ostreatus*) 9 desaturase." Abstract, Jun. 2005, National Plant Lipid Cooperative Meeting, California.

Thoguru JVSR, Rao SS, Hildebrand DF. "Production of Palmitoleic Acid." Abstract, May 2006. American Oil Chemists' Society Annual Meeting, St. Louis, MO.

Thoguru JVSR, Rao SS, Hildebrand DF. "A 16:0 active 9 desaturase gene from oyster mushroom (*Pleurotus ostreatus*)." Jul. 2006. 17th International Symposium on Plant Lipids, E. Lansing, MI.

\* cited by examiner

| | | | | | |
|---|---|---|---|---|---|
| *Ricinus communis* | GRVDMRQIEK | TIQYLIGSGM | DPRTENSPYL | GFIYTSFQER | ATFISHGNTA |
| *Asclepias syriaca* | GRVDMTMIDK | TIQYLLSSGM | NTGTNRNPYF | GFVYTSFQER | ATFVSHGNTA |
| *Brassica juncea* | GRVDMRQIEK | TIQYLIGSGM | DPRTENNPYL | GFIYTSFQER | ATFVSHGNTA |
| *Brassica napus* | GRVDMRQIEK | TIQYLIGSGM | DPRTENNPYL | GFVYTSFQER | ATFVSHGNTA |
| *Carthamus tinctorius* | GRVDMRQIQK | TIQYLIGSGM | DPRTENSPYL | GFVYTSFQER | ATFVSHGNTA |
| *Cucumis sativus* | GRVDMRQVEK | TIQYLIGSGM | DPRTENNPYL | GFVYTSFQER | ATFVSHGNTA |
| *Arachis hypogaea* | GRVDLRQIEK | TIQYLIGSGM | DPRTENSPYL | GFVYTSFQER | ATFVSHGNTA |
| *Elaeis guineensis* | GRVDMKQIEK | TIQYLIGSGM | DPRTENSPYL | GFVYTSFQER | ATFVSHGNTA |
| *Thunbergia alata* | GRVDMKQIEK | TIQYLIGSGM | DGADNNPYL | AYIYTSYQER | ATAISHGSLG |
| *Homo sapiens* | TFLRYAVVLN | ATWLVNS* | *AAHLF | GYRPYDKN | ISPRENILVS |
| *Rattus norvegicus* | TFLRYTLVLN | ATWLVNS* | *AAHLY | GYRPYDKN | IQSRENILVS |
| *Caenorhabditis elegans a* | ALFRYCFTLH | ATWCINS* | *VSHWV | GWQPYDHQ | ASSVDNLWTS |
| *Caenorhabditis elegans b* | GTFRYCFTLH | ATWCINS* | *AAHYF | GWKPYDTS | VSAVENVFTT |
| *Caenorhabditis elegans c* | GTFRYCFTLH | ATWCINS* | *AAHYF | GWKPYDSS | ITPVENVFTT |
| *Saccharomyces cerevisiae* | GHRVFVIQQ | ATFCINS* | *MAHYI | GTQPFDDR | RTPRDNWITA |
| *Pichia angusta* | GLLRAVFIQQ | ATFCVNS* | *LAHWI | GEQPFDDR | RTPRDHILTA |
| *Cryptococcus curvatus* | GAARLVFVHH | STFCVNS* | *LAHWL | GETPFDNK | HTPKDHFITA |
| *Amylomyces rouxii* | GVLRLCFVHH | ATFCVNS* | *LAHYL | GESTFDDH | NTPRDSWVTA |
| *P. ostreatus* | GMRLLTIAHH | STFCINS* | *IAHYL | GSTPYDDA | LTPRDHFLSA |

FIGURE 5

```
               1                                                      55
Po cDNA   (1)  ATGTCCAGAGAGCCAGAGTTGACATTGAAGCGCTGCAAGCATCTACATCGACGCT
Po gDNA   (1)  ATGTCCAGAGAGCCAGAGTTGACATTGAAGCGCTGCAAGCATCTACATCGACGCT
               56                                                     110
Po cDNA  (56)  CAGCACCCTACTGCCTCCAGGGTACCGATCGCAGGAGGCATTACTCTAATATGGC
Po gDNA  (56)  CACCACCCTACTGCCTCCAGGGTACCGATCGCAGGAGGCATTACTCTAATATGGC
               111                                                    165
Po cDNA (111)  AGCCCAACTACCGCCCTCTTCGCTCCCGTTCGTCCAAGGCGTCCGGTGGTTCAAT
Po gDNA (111)  AGCCCAACTACCGCCCTCTTCGCTCCCGTTCGTCCAAGGCGTCCGGTGCTTCAAT
               166                                                    220
Po cDNA (166)  GTCGCCGTCCTCACTATTACACCAAGCGTTGCAGTCTGGGGTCTCATGCATGTAC
Po gDNA (166)  GTCGCCGTCCTCACTATTACACCAAGCGTTGCAGTCTGGGGTCTCATGCATGTAC
               221                                                    275
Po cDNA (221)  CGTTTCAGGCAAGAACTCTCCTGTTCGCCGCAGCATACTACATATATTCGATGCT
Po gDNA (221)  CGTTTCAGGCAAGAACTCTCCTGTTCGCCGCAGCATACTACATATATTCGATGCT
               276                                                    330
Po cDNA (276)  AGG----------------------------------------------------
Po gDNA (276)  AGGTACGTCACAAGTGCTATCTTAAGTTCGCAGCTGCTCAGCACTACGCTACTAG
               331                                                    385
Po cDNA (279)  -CATTACCGCTGG------------------------------------------
Po gDNA (331)  GCATTACCGCTGGTCAGTCCGCGCCTAAACTTCGTACGCGTTTAATAAACATCTT
               386                                                    440
Po cDNA (291)  ------------------------ATATCATCGGCTGTGGTCCCACAGATCATA
Po gDNA (386)  CGTCTGACTATTGTCTTCACACAGGATATCATCGGCTGTGGTCCCACAGATCATA
               441                                                    495
Po cDNA (321)  TACGGCATCCTTCCCTTTACAATGTTTCCTGTTATTCGGCGGAACGAGTGCTGTG
Po gDNA (441)  TACGGCATCCTTCCCTTTACAATGTTTCCTGTTATTCGGCGGAACGAGTGCTGTG
               496                                                    550
Po cDNA (376)  CAAGGTTCTTGCTTCTGGTGGGCTCGCACGCACCGTTCCCACCATCGACATACAG
Po gDNA (496)  CAAGGTTCTTGCTTCTGGTGGGCTCGCACGCACCGTTCCCACCATCGACATACAG
               551                                                    605
Po cDNA (431)  ATACAGACTTCGATCCCTACAACGCCAAGCGCGGATCGTTCTGGACCCATGTTGG
Po gDNA (551)  ATACAGACTCCGATCCCTACAACGCCAAGCGCGGATTGTTCTGGACCCATGTTGG
               606                                                    660
Po cDNA (486)  ATGGATGCTCTTCAAAACGAACCTTCGCTCCGGCTCCGTCGACGCTTCCGACCTC
Po gDNA (606)  ATGGATGCTCTTCAAAACGAACCTTCGCTCCGGCTCCGTCGACGCTTCCGACCTC
               661                                                    715
Po cDNA (541)  CGAAATGACACCTTGCTTCAATGGCAACATACATGGTACATCTTCCTCGCAGCGT
Po gDNA (661)  CGAAATGACACCTTGCTTCAATGGCAACATACATGGTACATGTTCCTCGCAGCGT
               716                                                    770
Po cDNA (596)  TCTTCGGGTATCTTCTTCCCACCTTGGTACCCGGGATCGGGTGGGGAGACTGGTT
Po gDNA (716)  TCTTCGGGTATCTTCTTCCCACCTTGGTACCCGGGATCGGGTGGGGAGACTGGTT
               771                                                    825
Po cDNA (651)  GGGCGGGTTCTGCTTCTCGGGTATGCTTCGATTGACAATCGCACATCAC------
Po gDNA (771)  GGGCGGGTTCTGCTTCTCGGGTATGCTTCGATTGACAATCGCACATCACGTAAGT
```

FIGURE 9A (Cont.)

```
                    826                                                    880
Po cDNA    (700)   ------------------------------------------------------AGTACGTTT
Po gDNA    (826)   CAAGCGTCCGACATCCTATTTCTTAGCTGACTTCGACTTCTATTAGAGTACGTTT
                    881                                                    935
Po cDNA    (709)   TGCATAAACTCCATTGCTCATTACCTTGGCTCTACACCCTACGATGATGCGCTTA
Po gDNA    (881)   TGCATAAACTCCATTGCTCATTACCTTGGCTCTACACCCTACGATGATGCGCTTA
                    936                                                    990
Po cDNA    (764)   CGCCTCGCGATCATTTCCTATCCGCAATCCTCACCATGGGTGAAGGATATCATAA
Po gDNA    (936)   CGCCTCGCGATCATTTCCTATCCGCAATCCTCACCATGGGTGAAGGATATCATA-
                    991                                                    1045
Po cDNA    (819)   CTTCCATCATCAATTCCCATGGACTACAGAAATGCATTC-CGCTGGTACCAATA
Po gDNA    (990)   CTTTCATCATCA-TTCCCATGGACTACAGAAATGCATTTTCGCTGGTACCAATA
                    1046                                                   1100
Po cDNA    (873)   CGACCCAACGAAGTGGTTCATTGCCTTGTGTAACTTCATTGATCTGGCAGCCAAT
Po gDNA    (1044)  CGACCCAACGAAGTGGTTCATTGCCTTGTGTAACTTCATTGGTCTGGCAGCCAAT
                    1101                                                   1155
Po cDNA    (928)   CTGCGGGTGTTCCCCAGTAATGAGATTGACAAGGGTGTGTTGACAATGAAGCTCA
Po gDNA    (1099)  CTGCGGGTGTTCCCCAGTAATGAGATTGACAAGGGTGTGTTGACAATGAAGCTCA
                    1156                                                   1210
Po cDNA    (983)   AGGATCTGAAGCGAGAACAAGATCGGCTAAAATGGCCTGTCACAACTGAGAAGTT
Po gDNA    (1154)  AGGATCTGAAGCGAGAACAAGATCGGCTAAAATGGCCTGTCACAACTGAGAAGTT
                    1211                                                   1265
Po cDNA    (1038)  GCCAGTAGTGACATGGGAAACAT---------------------------------
Po gDNA    (1209)  GCCAGTAGTGACATGGGAAACATGTTAGTGAATTCGCCACAGCAATATATTTGTC
                    1266                                                   1320
Po cDNA    (1061)  -----------------------------TCCAGAAGGAGGCAGAGACATGC
Po gDNA    (1264)  GTGTCAAACTGATGATGCTGTGTTGCTACCAGTCCAGAAGGAGGCAGAGACATGC
                    1321                                                   1375
Po cDNA    (1084)  CCACTTTTGCTGATATCCGGGTTCATACACGATGTTTCGTTGTTTGTGGACCAGC
Po gDNA    (1319)  CCACTTTTGCTGATATCCCGGTTCATACACGATGTTTCGTTGTTTGTGGACCAGC
                    1376                                                   1430
Po cDNA    (1139)  ATCCTGGTGGACGTGGTACGCTTGAAAAGAATTCTGGGAAGGATATGACCGCTGC
Po gDNA    (1374)  ATCCTGGTGGACGTGGTACGCTTGAAAAGAATTCTGGGAAGGATATGACCGCTGC
                    1431                                                   1485
Po cDNA    (1194)  GTTCTTCGGAGGAGTTTATTCGCACTCACATGCCGCGCATAATTTGCTGTCCATG
Po gDNA    (1429)  GTTCTTCGGAGGAGTTTATTCGCACTCACATGCCGCGCATAATGTAC-GTG-ACG
                    1486                                                   1540
Po cDNA    (1249)  ATGCGAGTAGGCGTTCTTGACGGAGGCGTAGAGTTAAAATCACTAGTGAATTCGC
Po gDNA    (1482)  TTGC---------TTCTTG-CAGATACCTCGACCTACTCAC-CAAGTTCTTTGC
                    1541                                                   1595
Po cDNA    (1304)  GGCCGCCTGCAGGTCTGACCAT-ATGAGAGAGCTCCCAACGCGTGGATGCCATAG
Po gDNA    (1526)  AGTTGC---------TGTCCATGATGCGAGT------A-GGCGTTCTTGACGGA-
                    1596
Po cDNA    (1358)  CTTTTATAA
Po gDNA    (1564)  ---------
```

FIGURE 9B

MSREPELSLKRCKHLHRRSAPYCLQGTDRRRHYSNMAAQLPPSSLPFVQGVRWFNVAVLTI
TPSVAVWGLMHVPFQARTLLFAAAYYIYSMLGITAGYHRLWSHRSYTASFPLQCFLLFGGT
SAVQGCFWWRTHRSHHRHTDTDFDPYNAKRGSFWTHVGWMLFKTNLRSGSVDASDLRN
DTLLQWQHTWYMFLAAFFGYLLPTLVPGIGWGDWLGGFCFSGMLRLTIAHHSTFCINSIAH
YLGSTPYDDALTPDHFLSAILTMGEGYHNFHHQFPMDYRNAFRWYQYDPTKWFIALCNFID
LAANLRVFPSNEIDKGVLTMKLKDLKREQDRLKWPVTTEKLPVVTWETFQKEAETCPLLLIS
GFIHDVSLFVDQHPGGRTLEKNSGKDMTAAFFGGVYHSHAAHNLLSMMRVGVLDGGVEL
KSL

FIGURE 10

SEQUENCE LISTING

```
<160> NUMBER OF SEQ ID NOS: 50

<210> SEQ ID NO 1
<211> LENGTH: 1563
<212> TYPE: DNA
<213> ORGANISM: Pleurotus ostreatus

<400> SEQUENCE: 1
atgtccagag agccagagtt gacattgaag cgctgcaagc atctacatcg acgctcagca      60
ccctactgcc tccagggtac cgatcgcagg aggcattact ctaatatggc agcccaacta     120
ccgccctctt cgctcccgtt cgtccaaggc gtccggtggt tcaatgtcgc cgtcctcact     180
attacaccaa gcgttgcagt ctggggtctc atgcatgtac cgtttcaggc aagaactctc     240
ctgttcgccg cagcatacta catatattcg atgctaggta cgtcacaagt gctatcttaa     300
gttcgcagct gctcagcact acgctactag gcattaccgc tggtcagtcc gcgcctaaac     360
ttcgtacgcg tttaataaac atcttcgtct gactattgtc ttcacacagg atatcatcgg     420
ctgtggtccc acagatcata tacggcatcc ttcccttttac aatgtttcct gttattcggc     480
ggaacgagtg ctgtgcaagg ttcttgcttc tggtgggctc gcacgcaccg ttcccaccat     540
cgacatacag atacagactc cgatccctac aacgccaagc gcggattgtt ctggacccat     600
gttggatgga tgctcttcaa aacgaacctt cgctccggct ccgtcgacgc ttccgacctc     660
cgaaatgaca ccttgcttca atggcaacat acatggtaca tgttcctcgc agcgttcttc     720
gggtatcttc ttcccacctt ggtacccggg atcgggtggg gagactggtt gggcgggttc     780
tgcttctcgg gtatgcttcg attgacaatc gcacatcacg taagtcaagc gtccgacatc     840
ctatttctta gctgacttcg acttctatta gagtacgttt tgcataaact ccattgctca     900
ttaccttggc tctacaccct acgatgatgc gcttacgcct cgcgatcatt tcctatccgc     960
aatcctcacc atgggtgaag gatatcatac tttcatcatc attccccatg gactacagaa    1020
atgcattttc gctggtacca atacgaccca acgaagtggt tcattgcctt gtgtaacttc    1080
attggtctgg cagccaatct gcgggtgttc cccagtaatg agattgacaa gggtgtgttg    1140
acaatgaagc tcaaggatct gaagcgagaa caagatcggc taaaatggcc tgtcacaact    1200
gagaagttgc cagtagtgac atgggaaaca tgttagtgaa ttcgccacag caatatattt    1260
gtcgtgtcaa actgatgatg ctgtgttgct accagtccag aaggaggcag agacatgccc    1320
acttttgctg atatccgggt tcatacacga tgtttcgttg tttgtggacc agcatcctgg    1380
tggacgtggt acgcttgaaa agaattctgg gaaggatatg accgctgcgt tcttcggagg    1440
agtttattcg cactcacatg ccgcgcataa tgtacgtgac gttgcttctt gcagatacct    1500
```
cgacctactc accaagtttc tttgcagttg ctgtccatga tgcgagtagg cgttcttgac    1560
gga                                                                  1563

<210> SEQ ID NO 2
<211> LENGTH: 1366
<212> TYPE: DNA
<213> ORGANISM: Pleurotus ostreatus

<400> SEQUENCE: 2
atgtccagag agccagagtt gacattgaag cgctgcaagc atctacatcg acgctcagca      60
ccctactgcc tccagggtac cgatcgcagg aggcattact ctaatatggc agcccaacta     120
ccgcccctctt cgctcccgtt cgtccaaggc gtccggtggt tcaatgtcgc cgtcctcact    180
attacaccaa gcgttgcagt ctggggtctc atgcatgtac cgtttcaggc aagaactctc     240
ctgttcgccg cagcatacta catatattcg atgctaggca ttaccgctgg atatcatcgg     300
ctgtggtccc acagatcata tacggcatcc ttcccttttac aatgtttcct gttattcggc    360
ggaacgagtg ctgtgcaagg ttcttgcttc tggtgggctc gcacgcaccg ttcccaccat     420
cgacatacag atacagactt cgatccctac aacgccaagc gcggatcgtt ctggacccat    480
gttggatgga tgctcttcaa acgaaccctt cgctccggct ccgtcgacgc ttccgacctc     540
cgaaatgaca ccttgcttca atggcaacat acatggtaca tgttcctcgc agcgttcttc    600
gggtatcttc ttcccacctt ggtacccggg atcgggtggg agactggtt gggcgggttc     660
tgcttctcgg gtatgcttcg attgacaatc gcacatcaca gtacgttttg cataaactcc    720
attgctcatt accttggctc tacaccctac gatgatgcgc ttacgcctcg cgatcatttc    780
ctatccgcaa tcctcaccat gggtgaagga tatcataact ccatcatca attccccatg      840
gactacagaa atgcattccg ctggtaccaa tacgacccaa cgaagtggtt cattgccttg    900
tgtaacttca ttgatctggc agccaatctg cgggtgttcc ccagtaatga gattgacaag    960
ggtgtgttga caatgaagct caaggatctg aagcgagaac aagatcggct aaaatggcct   1020
gtcacaactg agaagttgcc agtagtgaca tgggaaacat tccagaagga ggcagagaca    1080
tgcccacttt tgctgatatc cgggttcata cacgatgttt cgttgtttgt ggaccagcat    1140
cctggtggac gtggtacgct tgaaaagaat tctgggaagg atatgaccgc tgcgttcttc    1200
ggaggagttt attcgcactc acatgccgcg cataatttgc tgtccatgat gcgagtaggc    1260
gttcttgacg gaggcgtaga gttaaaatca ctagtgaatt cgcggccgcc tgcaggtctg    1320
accatatgag agagctccca acgcgtggat gccatagctt ttataa                  1366

<210> SEQ ID NO 3
<211> LENGTH: 426
<212> TYPE: PRT
<213> ORGANISM: Pleurotus ostreatus

<400> SEQUENCE: 3

Met Ser Arg Glu Pro Glu Leu Ser Leu Lys Arg Cys Lys His Leu His
 1               5                  10                  15

Arg Arg Ser Ala Pro Tyr Cys Leu Gln Gly Thr Asp Arg Arg His
             20                  25                  30

Tyr Ser Asn Met Ala Ala Gln Leu Pro Pro Ser Ser Leu Pro Phe Val
         35                  40                  45

Gln Gly Val Arg Trp Phe Asn Val Ala Val Leu Thr Ile Thr Pro Ser
     50                  55                  60

Val Ala Val Trp Gly Leu Met His Val Pro Phe Gln Ala Arg Thr Leu

```
                65                  70                  75                  80
Leu Phe Ala Ala Ala Tyr Tyr Ile Tyr Ser Met Leu Gly Ile Thr Ala
                    85                  90                  95
Gly Tyr His Arg Leu Trp Ser His Arg Ser Tyr Thr Ala Ser Phe Pro
                    100                 105                 110
Leu Gln Cys Phe Leu Leu Phe Gly Gly Thr Ser Ala Val Gln Gly Cys
                    115                 120                 125
Phe Trp Trp Arg Thr His Arg Ser His His Arg His Thr Asp Thr Asp
                    130                 135                 140
Phe Asp Pro Tyr Asn Ala Lys Arg Gly Ser Phe Trp Thr His Val Gly
145                 150                 155                 160
Trp Met Leu Phe Lys Thr Asn Leu Arg Ser Gly Ser Val Asp Ala Ser
                    165                 170                 175
Asp Leu Arg Asn Asp Thr Leu Leu Gln Trp Gln His Thr Trp Tyr Met
                    180                 185                 190
Phe Leu Ala Ala Phe Phe Gly Tyr Leu Leu Pro Thr Leu Val Pro Gly
                    195                 200                 205
Ile Gly Trp Gly Asp Trp Leu Gly Gly Phe Cys Phe Ser Gly Met Leu
                    210                 215                 220
Arg Leu Thr Ile Ala His His Ser Thr Phe Cys Ile Asn Ser Ile Ala
225                 230                 235                 240
His Tyr Leu Gly Ser Thr Pro Tyr Asp Asp Ala Leu Thr Pro Asp His
                    245                 250                 255
Phe Leu Ser Ala Ile Leu Thr Met Gly Glu Gly Tyr His Asn Phe His
                    260                 265                 270
His Gln Phe Pro Met Asp Tyr Arg Asn Ala Phe Arg Trp Tyr Gln Tyr
                    275                 280                 285
Asp Pro Thr Lys Trp Phe Ile Ala Leu Cys Asn Phe Ile Asp Leu Ala
                    290                 295                 300
Ala Asn Leu Arg Val Phe Pro Ser Asn Glu Ile Asp Lys Gly Val Leu
305                 310                 315                 320
Thr Met Lys Leu Lys Asp Leu Lys Arg Glu Gln Asp Arg Leu Lys Trp
                    325                 330                 335
Pro Val Thr Thr Glu Lys Leu Pro Val Val Thr Trp Glu Thr Phe Gln
                    340                 345                 350
Lys Glu Ala Glu Thr Cys Pro Leu Leu Ile Ser Gly Phe Ile His
                    355                 360                 365
Asp Val Ser Leu Phe Val Asp Gln His Pro Gly Gly Arg Thr Leu Glu
                    370                 375                 380
Lys Asn Ser Gly Lys Asp Met Thr Ala Ala Phe Phe Gly Gly Val Tyr
385                 390                 395                 400
His Ser His Ala Ala His Asn Leu Leu Ser Met Met Arg Val Gly Val
                    405                 410                 415
Leu Asp Gly Gly Val Glu Leu Lys Ser Leu
                    420                 425

<210> SEQ ID NO 4
<211> LENGTH: 221
<212> TYPE: PRT
<213> ORGANISM: Pleurotus ostreatus

<400> SEQUENCE: 4

Ser Met Leu Gly Ile Thr Ala Gly Tyr His Arg Leu Trp Ser His Arg
1               5                   10                  15

Ser Tyr Thr Ala Ser Phe Pro Leu Gln Cys Phe Leu Leu Phe Gly Gly
```

```
                    20                  25                  30
Thr Ser Ala Val Gln Gly Cys Phe Trp Trp Arg Thr His Arg Ser His
                35                  40                  45
His Arg His Thr Asp Thr Asp Phe Asp Pro Tyr Asn Ala Lys Arg Gly
            50                  55                  60
Ser Phe Trp Thr His Val Gly Trp Met Leu Phe Lys Thr Asn Leu Arg
65                  70                  75                  80
Ser Gly Ser Val Asp Ala Ser Asp Leu Arg Asn Asp Thr Leu Leu Gln
                85                  90                  95
Trp Gln His Thr Trp Tyr Met Phe Leu Ala Ala Phe Phe Gly Tyr Leu
            100                 105                 110
Leu Pro Thr Leu Val Pro Gly Ile Gly Trp Gly Asp Trp Leu Gly Gly
            115                 120                 125
Phe Cys Phe Ser Gly Met Leu Arg Leu Thr Ile Ala His His Ser Thr
            130                 135                 140
Phe Cys Ile Asn Ser Ile Ala His Tyr Leu Gly Ser Thr Pro Tyr Asp
145                 150                 155                 160
Asp Ala Leu Thr Pro Asp His Phe Leu Ser Ala Ile Leu Thr Met Gly
                165                 170                 175
Glu Gly Tyr His Asn Phe His His Gln Phe Pro Met Asp Tyr Arg Asn
            180                 185                 190
Ala Phe Arg Trp Tyr Gln Tyr Asp Pro Thr Lys Trp Phe Ile Ala Leu
            195                 200                 205
Cys Asn Phe Ile Asp Leu Ala Ala Asn Leu Arg Val Phe
            210                 215                 220

<210> SEQ ID NO 5
<211> LENGTH: 11
<212> TYPE: PRT
<213> ORGANISM: Artificial Sequence
<220> FEATURE:
<223> OTHER INFORMATION: Homologous region in different fungal delta-9
      desaturase polypeptides
<220> FEATURE:
<221> NAME/KEY: X
<222> LOCATION: (10)..(10)
<223> OTHER INFORMATION: X is equal to serine or alanine

<400> SEQUENCE: 5

Ile Thr Ala Gly Tyr His Arg Leu Trp Xaa His
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Homologous region in different fungal delta-9
      desaturase polypeptides

<400> SEQUENCE: 6

Gly Glu Gly Tyr His Asn Phe His His
1               5

<210> SEQ ID NO 7
<211> LENGTH: 21
<212> TYPE: DNA
<213> ORGANISM: Artificial Sequence
<220> FEATURE:
<223> OTHER INFORMATION: Degenerate forward primer
<220> FEATURE:
<221> NAME/KEY: n
<222> LOCATION: (6)..(6)
```

```
<223> OTHER INFORMATION: n is equal to inosine
<220> FEATURE:
<221> NAME/KEY: y
<222> LOCATION: (9)..(9)
<223> OTHER INFORMATION: y is equal to any pyrimidine
<220> FEATURE:
<221> NAME/KEY: n
<222> LOCATION: (12)..(12)
<223> OTHER INFORMATION: n is equal to thymine or cytosine
<220> FEATURE:
<221> NAME/KEY: n
<222> LOCATION: (15)..(15)
<223> OTHER INFORMATION: n is equal to inosine
<220> FEATURE:
<221> NAME/KEY: n
<222> LOCATION: (18)..(18)
<223> OTHER INFORMATION: n is equal to any nucleotide including adenine,
      guanine, cytosine, thymine, or uracil

<400> SEQUENCE: 7
gccggntayc ancgnctntg g                                            21

<210> SEQ ID NO 8
<211> LENGTH: 21
<212> TYPE: DNA
<213> ORGANISM: Artificial Sequence
<220> FEATURE:
<223> OTHER INFORMATION: Degenerate forward primer
<220> FEATURE:
<221> NAME/KEY: n
<222> LOCATION: (6)..(6)
<223> OTHER INFORMATION: n is equal to inosine
<220> FEATURE:
<221> NAME/KEY: y
<222> LOCATION: (9)..(9)
<223> OTHER INFORMATION: y is equal to any pyrimidine
<220> FEATURE:
<221> NAME/KEY: y
<222> LOCATION: (12)..(12)
<223> OTHER INFORMATION: y is equal to any pyrimidine
<220> FEATURE:
<221> NAME/KEY: n
<222> LOCATION: (18)..(18)
<223> OTHER INFORMATION: n is equal to any nucleotide including adenine,
      guanine, cytosine, thymine, or uracil

<400> SEQUENCE: 8
gccggntayc ayagactntg g                                            21

<210> SEQ ID NO 9
<211> LENGTH: 21
<212> TYPE: DNA
<213> ORGANISM: Artificial Sequence
<220> FEATURE:
<223> OTHER INFORMATION: Degenerate forward primer
<220> FEATURE:
<221> NAME/KEY: n
<222> LOCATION: (6)..(6)
<223> OTHER INFORMATION: n is equal to inosine
<220> FEATURE:
<221> NAME/KEY: y
<222> LOCATION: (9)..(9)
<223> OTHER INFORMATION: y is equal to any pyrimidine
<220> FEATURE:
<221> NAME/KEY: n
<222> LOCATION: (12)..(12)
<223> OTHER INFORMATION: n is equal to thymine or cytosine
<220> FEATURE:
<221> NAME/KEY: n
<222> LOCATION: (15)..(15)
<223> OTHER INFORMATION: n is equal to inosine
<220> FEATURE:
<221> NAME/KEY: r
<222> LOCATION: (18)..(18)
<223> OTHER INFORMATION: r is equal to any purine
```

-continued

```
<400> SEQUENCE: 9
gccggntayc ancgnttrtg g                                             21

<210> SEQ ID NO 10
<211> LENGTH: 23
<212> TYPE: DNA
<213> ORGANISM: Artificial Sequence
<220> FEATURE:
<223> OTHER INFORMATION: Degenerate reverse primer
<220> FEATURE:
<221> NAME/KEY: r
<222> LOCATION: (6)..(6)
<223> OTHER INFORMATION: r is equal to any purine
<220> FEATURE:
<221> NAME/KEY: r
<222> LOCATION: (9)..(9)
<223> OTHER INFORMATION: r is equal to any purine
<220> FEATURE:
<221> NAME/KEY: r
<222> LOCATION: (15)..(15)
<223> OTHER INFORMATION: r is equal to any purine
<220> FEATURE:
<221> NAME/KEY: n
<222> LOCATION: (18)..(18)
<223> OTHER INFORMATION: n is equal to inosine
<220> FEATURE:
<221> NAME/KEY: y
<222> LOCATION: (21)..(21)
<223> OTHER INFORMATION: y is equal to any pyrimidine

<400> SEQUENCE: 10
tggtgraart tgtgrtancc ytc                                           23

<210> SEQ ID NO 11
<211> LENGTH: 23
<212> TYPE: DNA
<213> ORGANISM: Artificial Sequence
<220> FEATURE:
<223> OTHER INFORMATION: Inverse PCR primer

<400> SEQUENCE: 11
cttggctcta caccctacga tga                                           23

<210> SEQ ID NO 12
<211> LENGTH: 20
<212> TYPE: DNA
<213> ORGANISM: Artificial Sequence
<220> FEATURE:
<223> OTHER INFORMATION: Inverse PCR primer

<400> SEQUENCE: 12
ttgcacagca ctcgttccgc                                               20

<210> SEQ ID NO 13
<211> LENGTH: 21
<212> TYPE: DNA
<213> ORGANISM: Artificial Sequence
<220> FEATURE:
<223> OTHER INFORMATION: Forward primer for PCR

<400> SEQUENCE: 13
atccagagag ccagagttgt c                                             21

<210> SEQ ID NO 14
<211> LENGTH: 22
<212> TYPE: DNA
<213> ORGANISM: Artificial Sequence
<220> FEATURE:
<223> OTHER INFORMATION: Reverse primer for PCR
```

```
<400> SEQUENCE: 14
actctacgcc tccgtcaaga ac                                        22

<210> SEQ ID NO 15
<211> LENGTH: 24
<212> TYPE: DNA
<213> ORGANISM: Artificial Sequence
<220> FEATURE:
<223> OTHER INFORMATION: Forward primer for PCR

<400> SEQUENCE: 15
ctacgctgtc ggtggtgttt ctat                                      24

<210> SEQ ID NO 16
<211> LENGTH: 24
<212> TYPE: DNA
<213> ORGANISM: Artificial Sequence
<220> FEATURE:
<223> OTHER INFORMATION: Reverse primer for PCR

<400> SEQUENCE: 16
ctgaaagcct tggtagcgtc ctta                                      24

<210> SEQ ID NO 17
<211> LENGTH: 30
<212> TYPE: DNA
<213> ORGANISM: Artificial Sequence
<220> FEATURE:
<223> OTHER INFORMATION: Forward PCR primer for URA3 gene

<400> SEQUENCE: 17
ggtacccctg caggaaacga agataaatca                                30

<210> SEQ ID NO 18
<211> LENGTH: 30
<212> TYPE: DNA
<213> ORGANISM: Artificial Sequence
<220> FEATURE:
<223> OTHER INFORMATION: Reverse PCR primer for URA3 gene

<400> SEQUENCE: 18
tctagagggc gacacggaaa tgttgaatac                                30

<210> SEQ ID NO 19
<211> LENGTH: 32
<212> TYPE: DNA
<213> ORGANISM: Artificial Sequence
<220> FEATURE:
<223> OTHER INFORMATION: Forward primer for PCR

<400> SEQUENCE: 19
gaattcggcc gcaaattaaa gccttcgagc gt                             32

<210> SEQ ID NO 20
<211> LENGTH: 30
<212> TYPE: DNA
<213> ORGANISM: Artificial Sequence
<220> FEATURE:
<223> OTHER INFORMATION: Reverse primer for PCR

<400> SEQUENCE: 20
gaattcccca caaaccttca aatgaacgaa                                30

<210> SEQ ID NO 21
<211> LENGTH: 25
<212> TYPE: DNA
```

```
<213> ORGANISM: Artificial Sequence
<220> FEATURE:
<223> OTHER INFORMATION: Forward primer for PCR

<400> SEQUENCE: 21
atgccaactt ctggaactac tattg                                          25

<210> SEQ ID NO 22
<211> LENGTH: 26
<212> TYPE: DNA
<213> ORGANISM: Artificial Sequence
<220> FEATURE:
<223> OTHER INFORMATION: Reverse primer for PCR

<400> SEQUENCE: 22
ttaaaagaac ttaccagttt cgtaga                                         26

<210> SEQ ID NO 23
<211> LENGTH: 28
<212> TYPE: DNA
<213> ORGANISM: Artificial Sequence
<220> FEATURE:
<223> OTHER INFORMATION: Forward primer for PCR

<400> SEQUENCE: 23
atgaagcgct gcaagcatct acatcgac                                       28

<210> SEQ ID NO 24
<211> LENGTH: 25
<212> TYPE: DNA
<213> ORGANISM: Artificial Sequence
<220> FEATURE:
<223> OTHER INFORMATION: Reverse primer for PCR

<400> SEQUENCE: 24
ttaactctac gcctccgtca agaac                                          25

<210> SEQ ID NO 25
<211> LENGTH: 48
<212> TYPE: DNA
<213> ORGANISM: Artificial Sequence
<220> FEATURE:
<223> OTHER INFORMATION: Forward primer for PCR

<400> SEQUENCE: 25
agcgcatcat cgtagggtgt agacaaaagg taatgagcaa tggagttt                 48

<210> SEQ ID NO 26
<211> LENGTH: 48
<212> TYPE: DNA
<213> ORGANISM: Artificial Sequence
<220> FEATURE:
<223> OTHER INFORMATION: Reverse primer for PCR

<400> SEQUENCE: 26
aaactccatt gctcattacc ttttgtctac accctacgat gatgcgct                 48

<210> SEQ ID NO 27
<211> LENGTH: 45
<212> TYPE: DNA
<213> ORGANISM: Artificial Sequence
<220> FEATURE:
<223> OTHER INFORMATION: Forward primer for PCR

<400> SEQUENCE: 27
aactccttgg ctcattacat cttgacccaa ccattcgatg acaga                    45
```

-continued

```
<210> SEQ ID NO 28
<211> LENGTH: 45
<212> TYPE: DNA
<213> ORGANISM: Artificial Sequence
<220> FEATURE:
<223> OTHER INFORMATION: Reverse primer for PCR

<400> SEQUENCE: 28
tctgtcatcg aatggttggg tcaagatgta atgagccaag gagtt          45

<210> SEQ ID NO 29
<211> LENGTH: 6
<212> TYPE: PRT
<213> ORGANISM: Pleurotus ostreatus

<400> SEQUENCE: 29

His Arg Leu Trp Ser His
1               5

<210> SEQ ID NO 30
<211> LENGTH: 5
<212> TYPE: PRT
<213> ORGANISM: Pleurotus ostreatus

<400> SEQUENCE: 30

His Arg Ser His His
1               5

<210> SEQ ID NO 31
<211> LENGTH: 5
<212> TYPE: PRT
<213> ORGANISM: Pleurotus ostreatus

<400> SEQUENCE: 31

His Asn Phe His His
1               5

<210> SEQ ID NO 32
<211> LENGTH: 50
<212> TYPE: PRT
<213> ORGANISM: Ricinus communis

<400> SEQUENCE: 32

Gly Arg Val Asp Met Arg Gln Ile Glu Lys Thr Ile Gln Tyr Leu Ile
1               5                   10                  15

Gly Ser Gly Met Asp Pro Arg Thr Glu Asn Ser Pro Tyr Leu Gly Phe
            20                  25                  30

Ile Tyr Thr Ser Phe Gln Glu Arg Ala Thr Phe Ile Ser His Gly Asn
        35                  40                  45

Thr Ala
    50

<210> SEQ ID NO 33
<211> LENGTH: 50
<212> TYPE: PRT
<213> ORGANISM: Asclepias syriaca

<400> SEQUENCE: 33

Gly Arg Val Asp Met Thr Met Ile Asp Lys Thr Ile Gln Tyr Leu Leu
1               5                   10                  15

Ser Ser Gly Met Asn Thr Gly Thr Asn Arg Asn Pro Tyr Phe Gly Phe
            20                  25                  30

Val Tyr Thr Ser Phe Gln Glu Arg Ala Thr Phe Val Ser His Gly Asn
```

```
            35                  40                  45
Thr Ala
    50

<210> SEQ ID NO 34
<211> LENGTH: 50
<212> TYPE: PRT
<213> ORGANISM: Brassica juncea

<400> SEQUENCE: 34

Gly Arg Val Asp Met Arg Gln Ile Glu Lys Thr Ile Gln Tyr Leu Ile
1               5                  10                  15

Gly Ser Gly Met Asp Pro Arg Thr Glu Asn Asn Pro Tyr Leu Gly Phe
            20                  25                  30

Ile Tyr Thr Ser Phe Gln Glu Arg Ala Thr Phe Val Ser His Gly Asn
        35                  40                  45

Thr Ala
    50

<210> SEQ ID NO 35
<211> LENGTH: 50
<212> TYPE: PRT
<213> ORGANISM: Brassica napus

<400> SEQUENCE: 35

Gly Arg Val Asp Met Arg Gln Ile Glu Lys Thr Ile Gln Tyr Leu Ile
1               5                  10                  15

Gly Ser Gly Met Asp Pro Arg Thr Glu Asn Asn Pro Tyr Leu Gly Phe
            20                  25                  30

Val Tyr Thr Ser Phe Gln Glu Arg Ala Thr Phe Val Ser His Gly Asn
        35                  40                  45

Thr Ala
    50

<210> SEQ ID NO 36
<211> LENGTH: 50
<212> TYPE: PRT
<213> ORGANISM: Carthamus tinctorius

<400> SEQUENCE: 36

Gly Arg Val Asp Met Arg Gln Ile Gln Lys Thr Ile Gln Tyr Leu Ile
1               5                  10                  15

Gly Ser Gly Met Asp Pro Arg Thr Glu Asn Ser Pro Tyr Leu Gly Phe
            20                  25                  30

Val Tyr Thr Ser Phe Gln Glu Arg Ala Thr Phe Val Ser His Gly Asn
        35                  40                  45

Thr Ala
    50

<210> SEQ ID NO 37
<211> LENGTH: 50
<212> TYPE: PRT
<213> ORGANISM: Cucumis sativus

<400> SEQUENCE: 37

Gly Arg Val Asp Met Arg Gln Val Glu Lys Thr Ile Gln Tyr Leu Ile
1               5                  10                  15

Gly Ser Gly Met Asp Pro Arg Thr Glu Asn Asn Pro Tyr Leu Gly Phe
            20                  25                  30

Val Tyr Thr Ser Phe Gln Glu Arg Ala Thr Phe Val Ser His Gly Asn
```

```
                35                  40                  45
Thr Ala
    50

<210> SEQ ID NO 38
<211> LENGTH: 50
<212> TYPE: PRT
<213> ORGANISM: Arachis hypogaea

<400> SEQUENCE: 38

Gly Arg Val Asp Leu Arg Gln Ile Glu Lys Thr Ile Gln Tyr Leu Ile
1               5                   10                  15

Gly Ser Gly Met Asp Pro Arg Thr Glu Asn Ser Pro Tyr Leu Gly Phe
            20                  25                  30

Val Tyr Thr Ser Phe Gln Glu Arg Ala Thr Phe Val Ser His Gly Asn
        35                  40                  45

Thr Ala
    50

<210> SEQ ID NO 39
<211> LENGTH: 50
<212> TYPE: PRT
<213> ORGANISM: Elaeis guineensis

<400> SEQUENCE: 39

Gly Arg Val Asp Met Lys Gln Ile Glu Lys Thr Ile Gln Tyr Leu Ile
1               5                   10                  15

Gly Ser Gly Met Asp Pro Arg Thr Glu Asn Ser Pro Tyr Leu Gly Phe
            20                  25                  30

Val Tyr Thr Ser Phe Gln Glu Arg Ala Thr Phe Val Ser His Gly Asn
        35                  40                  45

Thr Ala
    50

<210> SEQ ID NO 40
<211> LENGTH: 49
<212> TYPE: PRT
<213> ORGANISM: Thunbergia alata

<400> SEQUENCE: 40

Gly Arg Val Asp Met Lys Gln Ile Glu Lys Thr Ile Gln Tyr Leu Ile
1               5                   10                  15

Gly Ser Gly Met Asp Gly Ala Asp Asn Asn Pro Tyr Leu Ala Tyr Ile
            20                  25                  30

Tyr Thr Ser Tyr Gln Glu Arg Ala Thr Ala Ile Ser His Gly Ser Leu
        35                  40                  45

Gly

<210> SEQ ID NO 41
<211> LENGTH: 40
<212> TYPE: PRT
<213> ORGANISM: Homo sapiens

<400> SEQUENCE: 41

Thr Phe Leu Arg Tyr Ala Val Val Leu Asn Ala Thr Trp Leu Val Asn
1               5                   10                  15

Ser Ala Ala His Leu Phe Gly Tyr Arg Pro Tyr Asp Lys Asn Ile Ser
            20                  25                  30

Pro Arg Glu Asn Ile Leu Val Ser
        35                  40
```

<210> SEQ ID NO 42
<211> LENGTH: 40
<212> TYPE: PRT
<213> ORGANISM: Rattus norvegicus

<400> SEQUENCE: 42

Thr Phe Leu Arg Tyr Thr Leu Val Leu Asn Ala Thr Trp Leu Val Asn
1               5                   10                  15

Ser Ala Ala His Leu Tyr Gly Tyr Arg Pro Tyr Asp Lys Asn Ile Gln
            20                  25                  30

Ser Arg Glu Asn Ile Leu Val Ser
        35                  40

<210> SEQ ID NO 43
<211> LENGTH: 40
<212> TYPE: PRT
<213> ORGANISM: Caenorhabditis elegans

<400> SEQUENCE: 43

Ala Leu Phe Arg Tyr Cys Phe Thr Leu His Ala Thr Trp Cys Ile Asn
1               5                   10                  15

Ser Val Ser His Trp Val Gly Trp Gln Pro Tyr Asp His Gln Ala Ser
            20                  25                  30

Ser Val Asp Asn Leu Trp Thr Ser
        35                  40

<210> SEQ ID NO 44
<211> LENGTH: 40
<212> TYPE: PRT
<213> ORGANISM: Caenorhabditis elegans

<400> SEQUENCE: 44

Gly Thr Phe Arg Tyr Cys Phe Thr Leu His Ala Thr Trp Cys Ile Asn
1               5                   10                  15

Ser Ala Ala His Tyr Phe Gly Trp Lys Pro Tyr Asp Thr Ser Val Ser
            20                  25                  30

Ala Val Glu Asn Val Phe Thr Thr
        35                  40

<210> SEQ ID NO 45
<211> LENGTH: 40
<212> TYPE: PRT
<213> ORGANISM: Caenorhabditis elegans

<400> SEQUENCE: 45

Gly Thr Phe Arg Tyr Cys Phe Thr Leu His Ala Thr Trp Cys Ile Asn
1               5                   10                  15

Ser Ala Ala His Tyr Phe Gly Trp Lys Pro Tyr Asp Ser Ser Ile Thr
            20                  25                  30

Pro Val Glu Asn Val Phe Thr Thr
        35                  40

<210> SEQ ID NO 46
<211> LENGTH: 40
<212> TYPE: PRT
<213> ORGANISM: Saccharomyces cerevisiae

<400> SEQUENCE: 46

Gly Phe Ile Arg Val Phe Val Ile Gln Gln Ala Thr Phe Cys Ile Asn
1               5                   10                  15

-continued

Ser Met Ala His Tyr Ile Gly Thr Gln Pro Phe Asp Asp Arg Arg Thr
            20                  25                  30

Pro Arg Asp Asn Trp Ile Thr Ala
        35                  40

<210> SEQ ID NO 47
<211> LENGTH: 40
<212> TYPE: PRT
<213> ORGANISM: Pichia angusta

<400> SEQUENCE: 47

Gly Leu Leu Arg Ala Val Phe Ile Gln Gln Ala Thr Phe Cys Val Asn
1               5                   10                  15

Ser Leu Ala His Trp Ile Gly Glu Gln Pro Phe Asp Asp Arg Arg Thr
            20                  25                  30

Pro Arg Asp His Ile Leu Thr Ala
        35                  40

<210> SEQ ID NO 48
<211> LENGTH: 40
<212> TYPE: PRT
<213> ORGANISM: Cryptococcus curvatus

<400> SEQUENCE: 48

Gly Ala Ala Arg Leu Val Phe Val His His Ser Thr Phe Cys Val Asn
1               5                   10                  15

Ser Leu Ala His Trp Leu Gly Glu Thr Pro Phe Asp Asn Lys His Thr
            20                  25                  30

Pro Lys Asp His Phe Ile Thr Ala
        35                  40

<210> SEQ ID NO 49
<211> LENGTH: 40
<212> TYPE: PRT
<213> ORGANISM: Amylomyces rouxii

<400> SEQUENCE: 49

Gly Val Leu Arg Leu Cys Phe Val His His Ala Thr Phe Cys Val Asn
1               5                   10                  15

Ser Leu Ala His Tyr Leu Gly Glu Ser Thr Phe Asp Asp His Asn Thr
            20                  25                  30

Pro Arg Asp Ser Trp Val Thr Ala
        35                  40

<210> SEQ ID NO 50
<211> LENGTH: 40
<212> TYPE: PRT
<213> ORGANISM: Pleurotus ostreatus

<400> SEQUENCE: 50

Gly Met Arg Leu Leu Thr Ile Ala His His Ser Thr Phe Cys Ile Asn
1               5                   10                  15

Ser Ile Ala His Tyr Leu Gly Ser Thr Pro Tyr Asp Asp Ala Leu Thr
            20                  25                  30

Pro Arg Asp His Phe Leu Ser Ala
        35                  40

FUNGAL DESATURASES AND RELATED METHODS

TECHNICAL FIELD

The presently-disclosed subject matter relates to fungal desaturases and methods of using the same. In particular, the presently-disclosed subject matter relates to novel nucleotide and amino acid sequences for mushroom desaturases and methods of using these sequences to produce monounsaturated fatty acids.

BACKGROUND

Plants naturally produce an assortment of fatty acids and synthesize a wide assortment of lipids, including mono-, di-, and tri-acylglycerols, phospholipids, glycolipids, and others, from the fatty acids produced by the plants. The specific assortment of lipids made by any particular plant is determined by both the genotype of the plant and the plant's response to environmental factors such as heat, cold, and drought. However, regardless of the environmental conditions a plant is faced with, a plant can never produce a fatty acid or lipid composition for which it does not have the necessary biochemical machinery.

Recently, there has been an increasing interest in reducing the content of saturated fatty acids in food for diet and health purposes. Medical and nutritional research continues to indicate that unsaturated fatty acids, such as those found in oilseed plants, are important components of diets for a variety of reasons. For example, certain monounsaturated fatty acids, such as palmitoleic acid, have been implicated in lowering the risk of cardiovascular and cerebrovascular diseases, in the regulation of immuno functions, and in the attenuation of inflammations. Efforts have therefore been initiated to develop oilseed varieties and plants which yield oils with higher monounsaturated fatty acid contents. However, the traditional methods of genetic modification of plants have involved recombination processes which are typically directed by the plant breeder at a whole plant level, and only produce incremental improvements in oil content and composition by optimizing the native biochemistry of a particular plant species, rather than considerably augmenting or introducing a biochemical pathway.

Further, even when traditional plant breeding methods are successful in altering the fatty acid composition of a particular plant variety, the native biochemical pathways of a plant will still generally exhibit all of their traditional characteristics and limitations. For example, the fatty acid compositions of many oilseed crops have been improved by plant breeding to include a higher content of unsaturated fatty acids. However, these oilseed crops continue to exhibit the usual response to environmental conditions such as a tendency to produce a higher percentage of saturated fatty acids under warmer growing conditions and a higher percentage of unsaturated fatty acids under cooler growing conditions, thus making the reliable production of oilseeds having a particular fatty acid composition difficult.

Accordingly, there remains a need in the art for compositions and methods useful for producing monounsaturated fatty acids.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments of the presently-disclosed subject matter, isolated nucleic acid and amino acid sequences are provided that encode a fungal desaturase polypeptide. In some embodiments, an isolated nucleic acid is provided that comprises a sequence that encodes a mushroom desaturase polypeptide or a functional fragment or functional variant thereof, where the mushroom desaturase is active with both palmitic acid and stearic acid. In some embodiments, the isolated nucleic acid comprises the sequence of SEQ ID NO: 1 or the sequence of SEQ ID NO: 2, or degenerate variants thereof. In some embodiments, the isolated nucleic acid encodes an amino acid sequence of SEQ ID NO: 3 or SEQ ID NO: 4, or functional fragments or functional variants thereof.

In some embodiments of the presently-disclosed subject matter, an isolated polypeptide is provided that comprises a mushroom desaturase polypeptide, or a functional fragment or functional variant thereof, that is active with both palmitic acid and stearic acid. In some embodiments, the polypeptide is isolated from *P. ostreatus*. In some embodiments, the polypeptide is a *P. ostreatus* Δ9 desaturase polypeptide. In some embodiments, the polypeptide has an amino acid sequence of SEQ ID NO: 3 or SEQ ID NO: 4, or functional fragments or functional variants thereof. In some embodiments, the polypeptide is encoded by a nucleic acid comprised of the sequence of SEQ ID NO: 1 or the sequence of SEQ ID NO: 2, or fragments thereof that are capable of encoding a functional fragment or functional variant of the polypeptide.

Further provided are vectors that comprise a nucleic acid of the presently-disclosed subject matter. In some embodiments, a vector is provided that comprises a nucleic acid comprising a sequence that encodes a mushroom desaturase. In some embodiments, the nucleic acid sequences can be operably linked to an expression cassette that can further include seed-specific or constitutive promoters.

In some embodiments of the presently-disclosed subject matter, transgenic plant cells are provided. In some embodiments, the transgenic plant cell is comprised of a nucleic acid of the presently-disclosed subject matter that encodes a mushroom desaturase polypeptide or a functional fragment or functional variant thereof. In some embodiments, the transgenic plant cell can be an *Arabidopsis* plant cell, a tobacco plant cell, a soybean plant cell, a petunia plant cell, a canola plant cell, a rapeseed plant cell, a palm plant cell, a sunflower plant cell, a cotton plant cell, a corn plant cell, a peanut plant cell, a flax plant cell, and a sesame plant cell.

The presently-disclosed subject matter further provides a method of producing a monounsaturated fatty acid. In some embodiments, the method comprises: transforming a cell with a nucleic acid of the presently-disclosed subject matter that encodes a mushroom desaturase polypeptide, or a functional fragment or a functional variant thereof, that is active with palmitic acid and stearic acid; expressing the desaturase polypeptide to increase an amount of the monounsaturated fatty acid in the cell; and, extracting an oil containing the increased amount of the monounsaturated fatty acid from the cell. In some embodiments, the monounsaturated fatty acid can be palmitoleic acid or oleic acid.

Still further provided are monounsaturated fatty acids that are prepared by the presently-disclosed methods. In some embodiments, the monounsaturated fatty acids are prepared by a process that comprises: transforming a cell with a nucleic acid of the presently-disclosed subject matter that encodes a fungal desaturase polypeptide, or a functional fragment or a functional variant thereof, that is active with palmitic acid and stearic acid; expressing the desaturase polypeptide to increase an amount of the monounsaturated fatty acid in the cell; and, extracting an oil containing the increased amount of the monounsaturated fatty acid from the cell.

Advantages of the presently-disclosed subject matter will become evident to those of ordinary skill in the art after a study of the description, Figures, and non-limiting Examples in this document.

BRIEF DESCRIPTION OF THE DRAWINGS

FIG. 5 is a chart depicting a glycine 188 residue (underlined) that is conserved in both acyl-CoA and acyl-ACP desaturases (SEQ ID NOS: 32-50) from a variety of organisms.

FIGS. 9A and 9B show the alignment of a genomic nucleic acid sequence (Po gDNA; SEQ ID NO: 1) and a cDNA sequence (Po cDNA; SEQ ID NO: 2) of a *P. ostreatus* Δ9 desaturase gene. FIG. 9A includes nucleic acids 1 to 825 and FIG. 9B includes nucleic acids 826 to 1604 of the genomic nucleic acid sequence, wherein the aligned nucleic acids of the cDNA sequence are presented immediately above the genomic nucleic acid sequence. Homology between the two sequences is indicated by the highlighted areas.

FIG. 10 includes an amino acid sequence of a full length *P. ostreatus* Δ9 desaturase polypeptide (SEQ ID NO: 3), wherein histidine residues corresponding to locations of histidine box motifs are presented in bold.

BRIEF DESCRIPTION OF THE SEQUENCE LISTING

Figure 1:
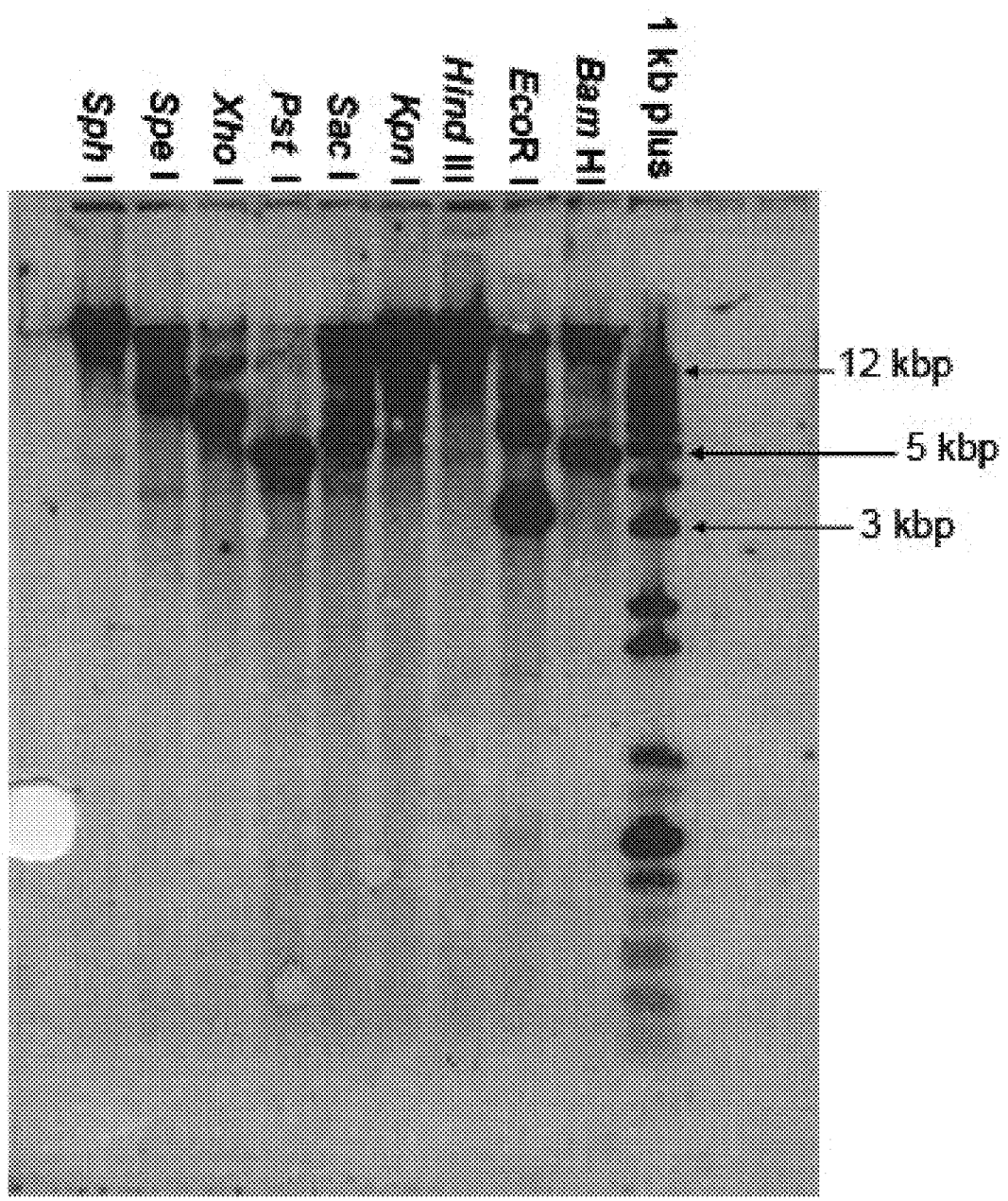
FIG. 1 is a picture depicting the southern hybridization of *P. ostreatus* genomic DNA probed with a 550 bp Δ9 desaturase specific PCR fragment. Depending on the restriction enzyme used to digest the genomic DNA, 1-4 strong bands are visible in the southern blot hybridization.

SEQ ID NO: 1 is a genomic nucleic acid sequence from *P. ostreatus*.

SEQ ID NO: 2 is a nucleic acid sequence of a cDNA obtained from *P. ostreatus*.

SEQ ID NO: 3 is an amino acid sequence of a full length *P. ostreatus* Δ9 desaturase polypeptide.

SEQ ID NO: 4 is an amino acid sequence of a desaturase portion of a *P. ostreatus* Δ9 desaturase polypeptide.

SEQ ID NO: 5 is an amino acid sequence of a homologous region of different fungal Δ9 desaturase proteins used to design a forward primer for degenerate PCR.

SEQ ID NO: 6 is an amino acid sequence of a homologous region of different fungal Δ9 desaturase proteins used to design a reverse primer for degenerate PCR.

SEQ ID NO: 7 is a nucleic acid sequence of a forward primer for degenerate PCR reactions used to amplify portions of a *P. ostreatus* Δ9 desaturase gene.

SEQ ID NO: 8 is a nucleic acid sequence of a forward primer for degenerate PCR reactions used to amplify portions of a *P. ostreatus* Δ9 desaturase gene.

SEQ ID NO: 9 is a nucleic acid sequence of a forward primer for degenerate PCR reactions used to amplify portions of a *P. ostreatus* Δ9 desaturase gene.

SEQ ID NO: 10 is a nucleic acid sequence of a reverse primer for degenerate PCR reactions used to amplify portions of a *P. ostreatus* Δ9 desaturase gene.

SEQ ID NO: 11 is a nucleic acid sequence of an inverse PCR primer for obtaining a 3' extension of a 500 bp product of a portion of a *P. ostreatus* Δ9 desaturase gene.

SEQ ID NO: 12 is a nucleic acid sequence of an inverse PCR primer for obtaining a 5' extension of a 500 bp product of a portion of a *P. ostreatus* Δ9 desaturase gene.

SEQ ID NO: 13 is a nucleic acid sequence of a forward PCR primer for amplifying a *P. ostreatus* Δ9 desaturase gene from *P. ostreatus* genomic DNA and total RNA.

SEQ ID NO: 14 is a nucleic acid sequence of a reverse PCR primer for amplifying a *P. ostreatus* Δ9 desaturase gene from *P. ostreatus* genomic DNA and total RNA.

SEQ ID NO: 15 is a nucleic acid sequence of a forward PCR primer for amplifying a *S. cerevisiae* Δ9 desaturase gene.

SEQ ID NO: 16 is a nucleic acid sequence of a reverse PCR primer for amplifying a *S. cerevisiae* Δ9 desaturase gene.

SEQ ID NO: 17 is a nucleic acid sequence of a forward PCR primer for amplifying a *S. cerevisiae* URA3 gene from a pYES2 expression vector.

SEQ ID NO: 18 is a nucleic acid sequence of a reverse PCR primer for amplifying a *S. cerevisiae* URA3 gene from a pYES2 expression vector.

SEQ ID NO: 19 is a nucleic acid sequence of a forward PCR primer for amplifying a construct comprised of a *S. cerevisiae* URA3 gene cloned into a pYES2 vector under a gal promoter.

SEQ ID NO: 20 is a nucleic acid sequence of a reverse PCR primer for amplifying a construct comprised of a *S. cerevisiae* URA3 gene cloned into a pYES2 vector under a gal promoter.

SEQ ID NO: 21 is a nucleic acid sequence of a forward PCR primer for amplifying a *S. cerevisiae* Δ9 desaturase gene.

SEQ ID NO: 22 is a nucleic acid sequence of a reverse PCR primer for amplifying a *S. cerevisiae* Δ9 desaturase gene.

SEQ ID NO: 23 is a nucleic acid sequence of a forward PCR primer for amplifying a *P. ostreatus* Δ9 desaturase gene from a *P. ostreatus* genomic clone.

SEQ ID NO: 24 is a nucleic acid sequence of a reverse PCR primer for amplifying a *P. ostreatus* Δ9 desaturase gene from a *P. ostreatus* genomic clone.

SEQ ID NO: 25 is a nucleic acid sequence of a forward PCR primer for site directed mutagenesis of a *P. ostreatus* Δ9 desaturase gene.

SEQ ID NO: 26 is a nucleic acid sequence of a reverse PCR primer for site directed mutagenesis of a *P. ostreatus* Δ9 desaturase gene.

SEQ ID NO: 27 is a nucleic acid sequence of a forward PCR primer for site directed mutagenesis of a *S. cerevisiae* Δ9 desaturase gene.

SEQ ID NO: 28 is a nucleic acid sequence of a reverse PCR primer for site directed mutagenesis of a *S. cerevisiae* Δ9 desaturase gene.

SEQ ID NO: 29 is an amino acid sequence of a histidine box motif from a *P. ostreatus* Δ9 desaturase polypeptide.

SEQ ID NO: 30 is an amino acid sequence of a histidine box motif from a *P. ostreatus* Δ9 desaturase polypeptide.

SEQ ID NO: 31 is an amino acid sequence of a histidine box motif from a *P. ostreatus* Δ9 desaturase polypeptide.

SEQ ID NO: 32 is an amino acid sequence of a fragment of a desaturase polypeptide of *Ricinus communis*.

SEQ ID NO: 33 is an amino acid sequence of a fragment of a desaturase polypeptide of *Asclepias syriaca*.

SEQ ID NO: 34 is an amino acid sequence of a fragment of a desaturase polypeptide of *Brassica juncea*.

SEQ ID NO: 35 is an amino acid sequence of a fragment of a desaturase polypeptide of *Brassica napus*.

SEQ ID NO: 36 is an amino acid sequence of a fragment of a desaturase polypeptide of *Carthamus tinctorius*.

SEQ ID NO: 37 is an amino acid sequence of a fragment of a desaturase polypeptide of *Cucumis sativus*.

SEQ ID NO: 38 is an amino acid sequence of a fragment of a desaturase polypeptide of *Arachis hypogaea*.

SEQ ID NO: 39 is an amino acid sequence of a fragment of a desaturase polypeptide of *Elaeis guineensis*.

SEQ ID NO: 40 is an amino acid sequence of a fragment of a desaturase polypeptide of *Thunbergia alata*.

SEQ ID NO: 41 is an amino acid sequence of a fragment of a desaturase polypeptide of *Homo sapiens*.

SEQ ID NO: 42 is an amino acid sequence of a fragment of a desaturase polypeptide of *Rattus norvegicus*.

SEQ ID NO: 43 is an amino acid sequence of a fragment of a desaturase polypeptide of *Caenorhabditis elegans* a.

SEQ ID NO: 44 is an amino acid sequence of a fragment of a desaturase polypeptide of *Caenorhabditis elegans* b.

SEQ ID NO: 45 is an amino acid sequence of a fragment of a desaturase polypeptide of *Caenorhabditis elegans* c.

SEQ ID NO: 46 is an amino acid sequence of a fragment of a desaturase polypeptide of *Saccharomyces cerevisiae*.

SEQ ID NO: 47 is an amino acid sequence of a fragment of a desaturase polypeptide of *Pichia angusta*.

SEQ ID NO: 48 is an amino acid sequence of a fragment of a desaturase polypeptide of *Cryptococcus curvatus*.

SEQ ID NO: 49 is an amino acid sequence of a fragment of a desaturase polypeptide of *Amylomyces rouxii*.

SEQ ID NO: 50 is an amino acid sequence of a fragment of a desaturase polypeptide of *P. ostreatus*.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polynucleotide and polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein. Unless otherwise indicated or apparent, the references to the GENBANK® database are references to the most recent version of the database as of the filing date of this Application.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly-understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The term "fatty acid" is used herein to refer to long chain aliphatic acids of varying carbon chain lengths. Generally, the term "fatty acid" is used to describe fatty acids comprising about 12 to about 22 carbon atoms with the predominant chain lengths being from about 16 to about 22 carbon atoms, although both longer and shorter chain lengths are known in the art. The structure of a fatty acid is represented herein by a notation system of "X:Y", where X is the total number of carbon (C) atoms and Y is the number of double bonds. Typically, fatty acids are classified as either saturated or unsaturated fatty acids.

The term "saturated fatty acids" refers to those fatty acids that have no double bonds between the carbon atoms in their backbone. In contrast, "unsaturated fatty acids" are cis-isomers that have double bonds along their carbon backbones. "Monounsaturated fatty acids" have only one double bond along the carbon backbone (e.g., between the 9th and 10th carbon atom for palmitoleic acid (16:1) and oleic acid (18:1)), while "polyunsaturated fatty acids" have at least two double bonds along their carbon backbone (e.g., between the 9th and 10th, and 12th and 13th carbon atoms for linoleic acid (18:2); and between the 9th and 10th, 12th and 13th, and 15th and 16th carbons atoms for α-linoleic acid (18:3)).

The term "desaturase" is used herein to refer to a polypeptide capable of catalyzing the desaturation (i.e. the introduction of a double bond) of one or more fatty acids to produce an unsaturated fatty acid of interest. For example, a Δ9 desaturase catalyzes the conversion of palmitic acid (16:0) to palmitoleic acid (16:1) and/or stearic acid (18:0) to oleic acid (18:1). In this regard, a desaturase can be said to be "active with" a fatty acid, the desaturation of which it catalyzes. For example, a Δ9 desaturase can be said to be active with palmitic acid (16:0) and stearic acid (18:0) because it can catalyze the conversion of palmitic acid (16:0) to palmitoleic acid (16:1) and/or stearic acid (18:0) to oleic acid (18:1). Examples of other desaturases include, but are not limited to, Δ8 desaturases that catalyze the conversion of eicosadienoic acid (20:2) to dihomo-γ-linoleic acid (20:3) and/or eicosatrienoic acid (20:3) to eicosatetraenoic acid (20:4), Δ5 desaturases that catalyze the conversion of dihomo-γ-linoleic acid (20:3) to arachidonic acid (20:4) and/or eicosatetraenoic acid (20:4) to eicosapentanoic acid (20:5), Δ6 desaturases that catalyze the conversion of linoleic acid (18:2) to γ-linoleic acid (18:3) and/or α-linoleic acid (18:3) to stearidonic acid (18:4), Δ4 desaturases that catalyze the conversion of docosapentanoic acid (22:5) to docosahexanoic acid (22:6), Δ12 desaturases that catalyze the conversion of oleic acid (18:1) to linoleic acid (18:2); Δ15 desaturases that catalyze the conversion of linoleic acid (18:2) to α-linoleic acid and/or γ-linoleic acid (18:3) to stearidonic acid (18:4), and Δ17 desaturases that catalyze the conversion of arachidonic acid (20:4) to eicosapentanoic acid by introducing a double bond between the $C_{17}$ and $C_{18}$ carbon atoms.

In animal and fungal cells, monounsaturated fatty acids are aerobically synthesized from saturated fatty acids by microsomal membrane-bound Δ9 fatty acid desaturases (1). The desaturation pathway starts by the introduction of a double bond between $C_9$ and $C_{10}$ of stearoyl-ACP (in plants) or stearoyl-CoA (in fungi and animals), producing oleoyl-thioesters (2). Most desaturases are endoplasmic reticulum (ER) membrane-bound diiron-oxo proteins and examination of deduced amino acid sequences for the membrane desaturases from mammals, fungi, insects, higher plants, and cyanobacteria has revealed three regions of conserved primary sequence containing eight histidine residues. The conserved histidine residues are important for coordinating two iron atoms at the active site of the desaturase on the cytosolic face of the ER, while hydrophobic residues form two membrane-spanning domains that anchor the protein in the lipid bilayer (3). Cytochrome b5 is used as the electron donor and in the majority of cases the desaturase is a protein fusion with a cytochrome b5 domain fused either at the N- or C-terminus (4).

Δ9 desaturase genes have been isolated from a number of organisms including Trypanosoma brucei, Hansenula polymorphs, Mortierella alpina, Cryptococcus curvatus, Lentinula edodes, Caenorhabditis elegans, Drosophila, and mice. Although fatty acid desaturation was first described using a yeast Δ9 desaturase system, only animal Δ9 enzymes have been successfully purified to homogeneity (5, 6). Further, expression of Δ9 desaturase is highly regulated in several organisms, including Saccharomyces cerevisiae, and this control is exerted both at the transcriptional and post-transcriptional level (7, 8). The Δ9 desaturase genes of M. alpina (4), P. angusta and Y. lipolytica (9) also show transcriptional regulation in response to supplementation with Δ9-unsaturated fatty acids although no such repression has been observed for K. thermotolerance or for S. kluveri (10). Similarly fatty acid analysis has shown that the ratio of palmitoleic acid to oleic acid was lower in S. kluveri (10) and M. alpina (4).

Despite the numerous reports regarding Δ9 desaturase genes, however, very few Δ9 desaturase proteins have been reported to have palmitic acid (16:0) specificity, much less specificity with both palmitic acid and stearic acid (18:0). For example, of the three C. elegans open reading frames that display Δ9 desaturase activity, only one of them readily desaturates palmitic acid, and the activity of this protein with stearic acid as a substrate has been reported to be very low (3). Further, of the fungal Δ9 desaturases reported thus far, the Saccharomyces cerevisiae Δ9 desaturase is the only enzyme that prefers palmitic acid as substrate.

Thus, there is presently an unmet need for fungal desaturases that are active with both palmitic acid and stearic acid substrates. Disclosed herein are nucleic acid and amino acid sequences for mushroom desaturase polypeptides that exhibit activity with both palmitic acid and stearic acid substrates. As disclosed herein in the Examples, it was ascertained that these novel sequences encoding mushroom desaturases can be used to transform plant cells and provide a method to increase the production of monounsaturated fatty acids within the plant cells. Accordingly, the presently-disclosed subject matter includes mushroom desaturase nucleic acid and amino acid sequences, as well as methods of using the same to produce monounsaturated fatty acids, such as palmitoleic acid and oleic acid.

In some embodiments of the presently-disclosed subject matter, an isolated nucleic acid is provided. In some embodiments, the isolated nucleic acid comprises a sequence encoding a mushroom desaturase polypeptide, or a functional fragment or functional variant thereof, that is active with palmitic acid and stearic acid. In some embodiments, an isolated nucleic acid is provided that comprises the sequence of SEQ ID NO: 1 or a degenerate variant of SEQ ID NO: 1. In some embodiments, and isolated nucleic acid is provided that comprises the sequence of SEQ ID NO: 2 or a degenerate variant of SEQ ID NO: 2.

The term "gene" is used broadly to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated.

The term "isolated", when used in the context of an isolated nucleic acid molecule or an isolated polypeptide, is a nucleic acid molecule or polypeptide that, by the hand of man, exists apart from its native environment and is therefore not a product of nature. An isolated nucleic acid molecule or polypeptide can exist in a purified form or can exist in a non-native environment such as, for example, in a transgenic host cell.

The term "degenerate variant" refers to a nucleic acid having a residue sequence that differs from a reference nucleic acid by one or more degenerate codon substitutions. Degenerate codon substitutions can be achieved by generating sequences in which the third position of one or more selected (or all) codons is substituted with mixed base and/or deoxyinosine residues (Batzer et al. (1991) *Nucleic Acid Res* 19:5081; Ohtsuka et al. (1985) *J Biol Chem* 260:2605 2608; Rossolini et al. (1994) *Mol Cell Probes* 8:91 98).

In some embodiments of the presently-disclosed subject matter, an isolated nucleic acid is provided that encodes an amino acid sequence of SEQ ID NO: 3 or a functional fragment or a functional variant of SEQ ID NO: 3. In some embodiments, an isolated nucleic acid is provided that encodes an amino acid sequence of SEQ ID NO: 4 or a functional fragment or a functional variant of SEQ ID NO: 4.

The terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 10, 20, 30, 40, 50, 60, 70, 80, 90, 100, 120, 140, 160, 180 200, 210, or 220 amino acids long.

Figure 2:
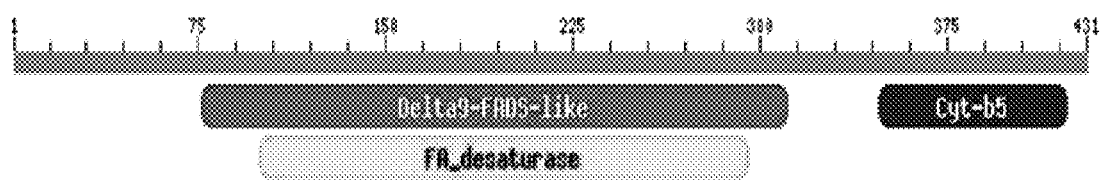
FIG. 2 is a diagram depicting the desaturase and cytochrome b5 portions of a *P. ostreatus* Δ9 desaturase polypeptide.

A fragment can also be a "functional fragment," in which case the fragment retains some or all of the activity of the reference polypeptide as described herein. For example, in some embodiments, a functional fragment of a mushroom desaturase polypeptide retains some or all of the ability of the reference polypeptide to desaturate a saturated fatty acid. As noted herein above and in FIG. 2, an exemplary mushroom desaturase polypeptide of the presently-disclosed subject matter can be described as being comprised of discrete domains including a desaturase domain and a cytochrome b5 domain. As such, in some embodiments, a functional fragment of a mushroom desaturase polypeptide can be a peptide that comprises the desaturase domain or a peptide that comprises a cytochrome b5 domain. As one exemplary embodiment of functional fragment of a mushroom desaturase polypeptide disclosed herein, the functional fragment of a mushroom desaturase polypeptide can be a polypeptide comprised of the desaturase domain, such as the polypeptide of SEQ ID NO: 4.

As noted above, fungal desaturase polypeptides of the presently-disclosed subject matter include mushroom desaturase polypeptides, which can comprise or consist essentially of a functional fragment of mushroom desaturase protein. A fragment can be identified with reference to amino acid residues in a reference polypeptide. For example, in some embodiments, a fragment can comprise or consist essentially of amino acids 90-310 of a full-length mushroom desaturase polypeptide, such as the polypeptide set forth in SEQ ID NO: 3. Such a fragment can be referred to as mushroom desaturase 90-310 or a 90-310 fragment.

In some embodiments, a polypeptide is provided that comprises a mushroom desaturase polypeptide comprising a fragment. In some embodiments, the fragment can begin at (i.e. extend from) about amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 52, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 of a full-length mushroom desaturase polypeptide, such as the polypeptide set forth in SEQ ID NO: 3. In some embodiments, the functional fragment can end at (i.e., extend to) about amino acid 350, 349, 348, 347, 346, 345, 344, 343, 342, 341, 340, 339, 338, 337, 336, 335, 334, 333, 332, 331, 330, 329, 328, 327, 326, 325, 324, 323, 322, 321, 320, 319, 318, 317, 316, 315, 314, 313, 312, 311, 310, 309, 308, 307, 306, 305, 304, 303, 302, 301, or 300 of a full-length mushroom desaturase polypeptide, such as the polypeptide set forth in SEQ ID NO: 3.

In some embodiments, the fragment begins at (i.e., extends from) about amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 52, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100; and ends at (i.e., extends to) about amino acid 350, 349, 348, 347, 346, 345, 344, 343, 342, 341, 340, 339, 338, 337, 336, 335, 334, 333, 332, 331, 330, 329, 328, 327, 326, 325, 324, 323, 322, 321, 320, 319, 318, 317, 316, 315, 314, 313, 312, 311, 310, 309, 308, 307, 306, 305, 304, 303, 302, 301, or 300 of a full-length mushroom desaturase polypeptide, such as the polypeptide set forth in SEQ ID NO: 3. In some embodiments, a mushroom desaturase polypeptide is provided that comprises or consists essentially of a mushroom desaturase fragment selected from 90-310 (SEQ ID NO: 4) and 75-345.

The terms "modified amino acid", "modified polypeptide", and "variant" refer to an amino acid sequence that is different from the reference polypeptide by one or more amino acids, e.g., one or more amino acid substitutions. A variant of a reference polypeptide also refers to a variant of a fragment of the reference polypeptide, for example, a fragment wherein one or more amino acid substitutions have been made relative to the reference polypeptide. A variant can also be a "functional variant," in which the variant retains some or all of the activity of the reference protein as described herein. For example, a functional variant of a mushroom desaturase polypeptide retains some or all of the ability of the reference polypeptide to desaturate a saturated fatty acid.

The term functional variant includes a functional variant of a functional fragment of a reference polypeptide. The term functional variant further includes conservatively substituted variants. The term "conservatively substituted variant" refers to a peptide comprising an amino acid residue sequence that differs from a reference peptide by one or more conservative amino acid substitutions, and maintains some or all of the activity of the reference peptide as described herein. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. The phrase "conservatively substituted variant" also includes peptides wherein a residue is replaced with a chemically derivatized residue, provided that the resulting peptide maintains some or all of the activity of the reference peptide as described herein.

Further provided, in some embodiments of the presently-disclosed subject matter, are isolated polypeptides. In some embodiments, an isolated polypeptide is provided that comprises a mushroom desaturase, or a functional fragment or a functional variant thereof, that is active with palmitic acid and stearic acid. In some embodiments, the polypeptide has an amino acid sequence of SEQ ID NO: 3 or SEQ ID NO: 4, or functional fragments or functional variants thereof. In some embodiments, the polypeptide is encoded by a nucleic acid that comprises a sequence of SEQ ID NO: 1 or that comprises a sequence of SEQ ID NO: 2 or degenerate variants thereof.

In some embodiments, an isolated polypeptide is provided that is isolated from *P. ostreatus*. The oyster mushroom, *P. ostreatus*, is an edible basidomycete of high nutritional value due to the high levels of vitamins, proteins, and unsaturated fatty acids found within the mushroom. *P. ostreatus* is produced industrially for the manufacture of paper pulp, cosmetics, and pharmaceuticals. However, the farming of oyster mushrooms is time and labor intensive, thus making the commercial cultivation of oyster mushrooms as a source of unsaturated fatty acids agronomically unfeasible. The inventors of the presently-disclosed subject matter have surprisingly discovered though that desaturase genes from *P. ostreatus* can be efficiently and economically used to produce desaturase polypeptides that are capable of increasing the accumulation of monounsaturated fatty acids in plants that can be grown on a commercial scale. As such, in some embodiments of the presently-disclosed subject matter, an isolated polypeptide is provided that is a *P. ostreatus* Δ9 desaturase polypeptide.

In some embodiments of the presently-disclosed subject matter, vectors that include one or more of the nucleic acid sequences disclosed herein are provided. In some embodiments, vectors are provided that comprise an nucleic acid sequence that encodes a mushroom desaturase polypeptide, or a functional fragment or a functional variant thereof, that is active with palmitic acid and stearic acid. For example, in some embodiments, the vectors can be comprised of a nucleic acid sequence comprising the sequence of SEQ ID NO: 1 or SEQ ID NO: 2, or degenerate variants thereof. As another example, in some embodiments, the vectors can be comprised of a nucleic acid sequence that encodes an amino acid sequence of SEQ ID NO: 3 or an amino acid sequence of SEQ ID NO: 4, or functional fragments or functional variants thereof.

The term "vector" is used herein to refer to any vehicle that is capable of transferring a nucleic acid sequence into another cell. For example, vectors which can be used in accordance with the presently-disclosed subject matter include, but are not limited to, plasmids, cosmids, bacteriophages, or viruses, which can be transformed by the introduction of a nucleic acid sequence of the presently-disclosed subject matter. Such vectors are well known to those of ordinary skill in the art. As one exemplary embodiment of a vector comprising a nucleic acid sequence of the presently disclosed subject matter, an exemplary vector can be a plasmid, such as the plasmid pCAMBIA 1301, into which a nucleic acid encoding a mushroom desaturase polypeptide can be cloned by the use of internal restriction sites present within the vector.

In some embodiments, the nucleic acids of the presently-disclosed subject matter are operably linked to an expression cassette. The terms "associated with", "operably linked", and "operatively linked" refer to two nucleic acid sequences that are related physically or functionally. For example, a promoter or regulatory DNA sequence is said to be "associated with" a DNA sequence that encodes an RNA or a polypeptide if the two sequences are operatively linked, or situated such that the regulator DNA sequence will affect the expression level of the coding or structural DNA sequence.

The term "expression cassette" refers to a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression.

In some embodiments, an expression cassette is provided that comprises a "constitutive promoter," such as a 35S promoter, a figwort mosaic promoter, or the constitutive plant promoter of ubiquitin, that continually expresses a nucleic acid sequence of the presently-disclosed subject matter in all types of cells where it is inserted. For some applications, it is useful to direct the expression of a nucleic acid sequence of the presently-disclosed subject matter to different tissues of a plant. As such, in some embodiments, an expression cassette is provided that comprises a "seed-specific promoter," such as a phaseolin, glycinin, conglycinin, seed lectin, napin, cruferin, or other seed-specific promoter, that expresses a nucleic acid sequence of the presently-disclosed subject matter only in seeds of a desired plant.

The presently-disclosed subject matter also provides transgenic plant cells or plants that comprise one or more of the nucleic acids disclosed herein. As used herein, the term "plant cell" is understood to mean any cell derived from a monocotyledonous or a dicotyledonous plant and capable of constituting undifferentiated tissues such as calli, differentiated tissues such as embryos, portions of monocotyledonous plants, monocotyledonous plants or seed. The term "plant" is understood to mean any differentiated multicellular organism capable of photosynthesis, including monocotyledons and dicotyledons. In some embodiments, the plant cell can be an *Arabidopsis* plant cell, a tobacco plant cell, a soybean plant cell, a petunia plant cell, or a cell from another oilseed crop including, but not limited to, a canola plant cell, a rapeseed plant cell, a palm plant cell, a sunflower plant cell, a cotton plant cell, a corn plant cell, a peanut plant cell, a flax plant cell, and a sesame plant cell.

The terms "transformed", "transgenic", and "recombinant" refer to a cell of a host organism such as a plant into which a heterologous nucleic acid molecule has been introduced. The nucleic acid molecule can be stably integrated into the genome of the cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "heterologous", "recombinant", and "exogenous", when used herein to refer to a nucleic acid sequence (e.g. a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found. Similarly, when used in the context of a polypeptide or amino acid sequence, an exogenous polypeptide or amino acid sequence is a polypeptide or amino acid sequence that originates from a source foreign to the particular host cell or, if from the same source, is modified from its original form. Thus, exogenous DNA segments can be expressed to yield exogenous polypeptides.

Introduction of a nucleic acid of the presently-disclosed subject matter into a plant cell can be performed by a variety of methods known to those of ordinary skill in the art including, but not limited to, insertion of a nucleic acid sequence of interest into an *Agrobacterium rhizogenes* Ri or *Agrobacterium tumefaciens* Ti plasmid, microinjection, electroporation, or direct precipitation. By way of providing another example, in some embodiments, transient expression of a nucleic acid sequence or gene of interest can be performed by agroinfiltration methods. In this regard, a suspension of *Agrobacterium tumefaciens* containing a gene of interest can be grown in culture and then injected into a plant by placing the tip of a syringe against the underside of a leaf while gentle counter-pressure is applied to the other side of the leaf. The *Agrobacterium* solution is then injected into the airspaces inside the leaf through stomata. Once inside the leaf, the *Agrobacterium* transforms the gene of interest to a portion of the plant cells where the gene is then transiently expressed.

As another example, transformation of a plasmid or nucleic acid of interest into a plant cell can be performed by particle gun bombardment techniques. In this regard, a suspension of plant embryos can be grown in liquid culture and then bombarded with plasmids or nucleic acids that are attached to gold particles, wherein the gold particles bound to the plasmid or nucleic acid of interest can be propelled through the membranes of the plant tissues, such as embryonic tissue. Following bombardment, the transformed embryos can then be selected using an appropriate antibiotic to generate new, clonally propagated, transformed embryogenic suspension cultures.

For additional guidance regarding methods of transforming and producing transgenic plant cells, see U.S. Pat. Nos. 4,459,355; 4,536,475; 5,464,763; 5,177,010; 5,187,073; 4,945,050; 5,036,006; 5,100,792; 5,371,014; 5,478,744; 5,179,022; 5,565,346; 5,484,956; 5,508,468; 5,538,877; 5,554,798; 5,489,520; 5,510,318; 5,204,253; 5,405,765; EP Nos. 267,159; 604,662; 672,752; 442,174; 486,233; 486,234; 539,563; 674,725; and, International Patent Application Publication Nos. WO 91/02071 and WO 95/06128, each of which is incorporated herein by this reference.

Still further provided, in some embodiments of the presently-disclosed subject matter, are methods of producing a monounsaturated fatty acid. In some embodiments, the method comprises: transforming a cell with a nucleic acid encoding a mushroom desaturase polypeptide, or a functional fragment or functional variant thereof, that is active with palmitic acid and stearic acid; expressing the desaturase polypeptide to thereby increase the amount of a the monounsaturated fatty acid in the cell; and, extracting an oil containing the increased amount of the monounsaturated fatty acid from the cell. In some embodiments, the monounsaturated fatty acid is palmitoleic acid or oleic acid.

The "amount" of a monounsaturated fatty acid in a cell can be determined by methods known to those of ordinary skill in the art. For example, gas chromatography-mass spectrometry or gas chromatography can be utilized to determine a total amount of monounsaturated fatty acids in a sample obtained from a cell transformed with a nucleic acid of the presently-disclosed subject matter. An increase in the amount of a monounsaturated fatty acid can then be measured relative to a control level of the monounsaturated fatty acid. The "control level" is an amount or range of amounts of the monounsaturated fatty acid found in a comparable samples in cells that have not been transformed with a nucleic acid of the presently-disclosed subject matter. In some embodiments, the increase in the amounts of the monounsaturated fatty acid can be about 1%, about 5%, about 8%, about 10%, about 15%, about 20%, about 25%, about 30%, about 40%, about 45%, or about 50%.

In some embodiments of the methods for producing a monounsaturated fatty acid, a cell is transformed with a nucleic acid of the presently-disclosed subject matter that is capable of expressing a polypeptide that is encoded by SEQ ID NO: 1 or SEQ ID NO: 2, or degenerate variants thereof. In some embodiments, the polypeptide is encoded by a nucleic acid sequence that encodes an amino acid sequence of SEQ ID NO: 3 or SEQ ID NO: 4, or functional fragments or functional variants thereof.

The methods of producing a monounsaturated fatty acid disclosed herein can be used to provide a monounsaturated fatty acid that can further be used in various food products or for industrial applications. As such, in some embodiments of the presently-disclosed subject matter a monounsaturated fatty acid is provided, such as a palmitoleic acid or an oleic acid.

In some embodiments, a monounsaturated fatty acid is provided that is prepared by a process that comprises: transforming a cell with a nucleic acid of the presently-disclosed subject matter encoding a fungal desaturase polypeptide, or functional fragment or functional variant thereof, that is active with palmitic acid and stearic acid; expressing the desaturase polypeptide to increase an amount of a monounsaturated fatty acid in a cell; and, extracting an oil containing the increased amount of the monounsaturated fatty acid from the cell. Extraction of an oil from a cell can be performed by a variety of methods known to those of ordinary skill in the art. For example, an oil containing an increased amount of a monounsaturated fatty acid can be extracted from a plant cell using a common solvent extraction or, alternatively, an oil containing an increased amount of a monounsaturated fatty acid can be extracted from a plant cell by pressing the oil out of plant cells and/or tissues and then collecting the oil in a suitable container.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Polynucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Materials and Methods for Examples 1-6

*P. ostreatus* Culture and Growth

An oyster mushroom (*P. ostreatus*) kit was obtained from Black Mountain Mushrooms, Guffey, Colo. The kit was placed in the lab at room temperature and was sprayed with water regularly as advised by the kit suppliers. After 2 weeks stalks and fruiting bodies of the well grown *P. ostreatus* were collected and stored at −80° C. until further use.

Isolation of DNA and RNA

*P. ostreatus* total DNA was isolated by homogenizing 100 mg of the fruiting bodies with mortar and pestle as previously described (12). *P. ostreatus* total RNA was isolated using TRIZOL® reagent (Invitrogen, Carlsbad, Calif.) as advised by the manufacturers.

Degenerate PCR

Based on the homology comparisons of different fungal Δ9 desaturase protein sequences two homologous regions, ITAGYHRLWS/AH (SEQ ID NO: 5) for forward and GEGYHNFHH (SEQ ID NO: 6) for reverse primer were identified. After careful comparison of the nucleic acid sequences different degenerate forward primers and a single degenerate reverse primer were designed. The forward primers were designated as (A), (B) & (C). The sequences used for the forward primers and the reverse primer were as follows; where R can be any purine, Y can be any pyrimidine, and, T/C indicates that either a thymine or cytosine molecule can occupy that position in the nucleic acid sequence:

```
                                           (SEQ ID NO: 7)
Prim-    5'-GCCGGITA(Y)CA(T/C)CGICT(N)TGG-3';
er A:

(SEQ ID NO: 8)
Primer B: 5'-GCCGGITA(Y)CA(Y)AGACT(N)TGG-3';

(SEQ ID NO: 9)
Primer C: 5'-GCCGGITA(Y)CA(T/C)CGITT(R)TGG-3';

(SEQ ID NO: 10)
Reverse  5'-TGGTG(R)AA(R)TTGTG(R)TAICC(Y)TC-3'.
primer:
```

Three separate PCR reactions were done with all three forward primers A, B & C. The PCR conditions for the reactions were 95'C for 5 min, 40 cycles of 95'C for 20 seconds, 45-55° C. temperature gradient for 30 seconds, 68° C. for 1 minute, and a final extension at 72° C. for 10 minutes. A 500 bp amplified product with primers A & B was obtained and then cloned into a pGEM-T vector (Amersham Biosciences, Piscataway, N.J., USA), and was then followed by sequencing.

Southern Blot Hybridization

Approximately 10 μg of *P. ostreatus* genomic DNA was digested overnight with BamHI, EcoR I, Hind III, Kpn I, Sac I, Pst I, Xho I, Spe I and Sph I restriction endonucleases. The digested DNA was separated on a 0.8% agarose gel and blotted onto Zetaprobe membrane (Bio-Rad Laboratories, Hercules, Calif.). The 500 bp Δ9 desaturase specific PCR fragment of *P. ostreatus* was random primed with $^{32}$P dCTP using the Prime-It II Random Primer labeling kit (Stratagene, La Jolla, Calif.). Hybridization was done overnight at 42° C. in formamide solution. The membrane was washed 3 times at 65° C. in 0.1×SSC and 0.1% sodium dodecyl sulfate (SDS) and exposed in a phosphor imager cassette (Molecular Dynamics, Sunnyvale, Calif.). The signal intensity was quantified using ImageQuant software (Molecular Dynamics, Sunnyvale, Calif.).

Southern blotting was carried out to determine which restriction enzymes to use for the digestion of the *P. ostreatus* genomic DNA. Previous data showed that the reported fungal Δ9 desaturase cDNAs were approximately of 1.3-1.5 kbp in length. BamHI, EcoR I and Pst I which contained hybridization bands of 3-5 kbp in size were chosen as restriction enzymes for the digestion of *P. ostreatus* genomic DNA for subsequent use in inverse-PCR. Other enzymes produced hybridization bands of 8-12 kbp in size and were avoided because of their large sizes.

Inverse-PCR

A 40 μg aliquot of *P. ostreatus* genomic DNA was digested with two different restriction enzymes BamHI and EcoRI independently at 37° C. for 16 h. The digested DNA was extracted with an equal volume of phenol: chloroform: isoamyl alcohol and the phases were separated by centrifugation for 5 min at 4° C. in a microcentrifuge. The DNA was precipitated with 1/10th volume of 3M sodium acetate, pH 5.5 and 2.5 volumes of absolute ethanol, followed by a 30 min incubation at −70° C. The DNA was pelleted by centrifugation, air dried and resuspended in 50 μl TE buffer (10 mM Tris-HCl, 1 mM EDTA, pH 8.0). The DNA was self-ligated for 18 h at 16° C. (13). The ligated DNA was extracted once with phenol/chloroform followed by extraction. Circular DNA was resuspended in 10 μl of TE buffer (pH 8.0) and used as template for inverse-PCR reaction. To clone the 5' and 3' flanking sequences of the approximately 500 bp amplified product primers directed away from one another were designed. The inverse -PCR primer 5'-CTTGGCTCTACAC-CCTACGATGA-3' (SEQ ID NO: 11) was used to obtain the 3' extension of the gene while the primer 5'-TTGCACAG-CACTCGTTCCGC-3' (SEQ ID NO: 12) was used to amplify the 5' end.

Two μl of the suspended DNA was used as template in a 50 μl inverse-PCR reaction. The PCR conditions were 95° C. for 5 min, 40 cycles of 95° C. for 20 seconds, 55° C. temperature for 30 seconds, 68° C. for 3 minutes and a final extension at 72° C. for 10 minutes. Products ranging from 0.8-1.6 kbp were amplified in the inverse-PCR reaction. Different amplified products were cloned into the pGEM-Teasy vector and sequenced. This sequence was used to design PCR primers to amplify the Δ9 desaturase gene from *P. ostreatus* genomic DNA and total RNA. The sequence of the forward primer was 5'-ATCCAGAGAGCCAGAGTTGTC-3' (SEQ ID NO: 13) and the sequence of the reverse primer was 5'-ACTCTACGC-CTCCGTCAAGAAC-3' (SEQ ID NO: 14). PCR and RT- PCR products of P. ostreatus Δ9 desaturase were then cloned into an appropriate vector, such as a pGEM-Teasy vector or pCAMBIA 1301 vector.

Yeast Δ9 Desaturase Auxotroph

A yeast Δ9 desaturase auxotroph was created to examine the function of the cloned gene. A 1.0 kbp portion of the S. cerevisiae Δ9 desaturase gene was amplified with a Δ9 desaturase forward primer 5'-CTACGCTGTCGGTGGT-GTTTCTAT-3' (SEQ ID NO: 15) and Δ9 desaturase reverse primer 5'-CTGAAAGCCTTGGTAGCGTCCTTA-3' (SEQ ID NO: 16). The amplified portion of the gene has two internal EcoRI sites. The amplified Δ9 desaturase product was cloned into a pGEMT-vector. The yeast (Saccharomyces cerevisiae.) URA3 gene, that codes for orotidine-5'-phosphate (OMP) decarboxylase, which is required for the synthesis of uracil, was amplified from the pYES2 yeast expression vector using the forward primer 5'-GGTACCCCTGCAGGAAAC-GAAGATAAATCA-3' (SEQ ID NO: 17) and reverse primer 5'-TCTAGAGGGCGACACGGAAATGTTGAATAC-3' (SEQ ID NO: 18). The amplified uracil gene was cloned into pGEM-T vector, digested with KpnI and HindIII and cloned into the multiple cloning site of the pYES2 vector under the gal promoter. The whole construct was amplified with the forward 5'-GAATTCGGCCGCAAATTAAAGCCTTC-GAGCGT-3' (SEQ ID NO: 19) and reverse 5'-GAATTC-CCCACAAACCTTCAAATGAACGAA-3' (SEQ ID NO: 20) primers with an EcoRI restriction site introduced at the ends. The amplified product was cloned into the pGEM-T vector. The URA3 gene with the gal promoter and terminator was digested with EcoRI and cloned into the EcoRI digested Δ9 desaturase -pGEM-T vector. The resulting clone consisted of a portion of Δ9 desaturase hanging on either side of the uracil gene with the gal promoter and terminator. The PCR product amplified with the Δ9 desaturase primers was used to transform the yeast auxotroph.

Cloning of the P. ostreatus and S. cerevisiae Δ9 Desaturase Genes into the pYES2 Yeast Expression Vector The S. cerevisiae Δ9 desaturase gene was amplified with the Δ9 desaturase forward primer 5'-ATGCCAACTTCTG-GAACTACTATTG-3' (SEQ ID NO: 21) and Δ9 desaturase reverse primer 5'-TTAAAAGAACTTACCAGTTTCG-TAGA-3' (SEQ ID NO: 22). The amplified Δ9 desaturase product was cloned into a T-vector digested with the Not I restriction enzyme and cloned into the Not I cloning site of the pYES2 vector under the gal promoter. The P. ostreatus genomic clone was amplified using the forward primer 5'-AT-GAAGCGCTGCAAGCATCTACATCGAC-3' (SEQ ID NO: 23) and Δ9 desaturase reverse primer 5'-TTAACTCTACGC-CTCCGTCAAGAAC-3' (SEQ ID NO: 24). The P. ostreatus Δ9 desaturase was digested from the T-vector with Not I and cloned into the Not I site of the pYES2 vector as described for the S. cerevisiae Δ9 desaturase cloning into the same vector.

Functional Assay

The Δ9 desaturase disrupted S. cerevisiae strain InVSc-1 (Invitrogen, Carlsbad, Calif.) requires a supplement of unsaturated fatty acids for growth. The mutant cells were grown in YPD medium (2% Bacto peptone, 1% yeast extract, 2% glucose) containing 0.5 mM oleic acid and 0.5 mM palmitoleic acid (Sigma, St Louis, Mo.) as well as 1% Tergitol, (Sigma, St. Louis, Mo.) to solubilize the unsaturated fatty acids. Competent yeast cells were made and transformed according to a previously described protocol (14) with the pYES2-Δ9 desaturase clones of P. ostreatus and S. cerevisiae. The transformed cells were plated onto complete minimal medium containing galactose but lacking uracil and fatty acids. A Δ9 desaturase auxotroph wherein the whole Δ9 desaturase gene was deleted was also obtained (Dr. Mendenhall, University of Kentucky, Lexington, USA). Both auxotrophs with the P. ostreatus Δ9 desaturase and also the S. cerevisiae Δ9 desaturase, which was used as a positive control (15), were successfully rescued.

Site Directed Mutagenesis

Site directed mutagenesis of the P. ostreatus and S. cerevisiae Δ9 desaturase genes were accomplished with the QUICKCHANGE® II site directed mutagenesis kit (Stratagene). The primers used for the QUICKCHANGE PCR for P. ostreatus were 5'-AGCGCATCATCGTAGGGTGTAGA-CAAAAGGTAATGAGCAATGGAGTTT-3' (SEQ ID NO: 25) and 5'-AAACTCCATTGCTCATTACCTTTTGTC-TACACCCTACGATGATGCGCT-3' (SEQ ID NO: 26) and for the S. cerevisiae Δ9 desaturase were 5'-AACTCCTTG-GCTCATTACATCTTGACCCAACCATTCGATGACAGA-3' (SEQ ID NO: 27) and 5-'TCTGTCATCGAATGGT-TGGGTCAAGATGTAATGAGCCAAGGAGTT-3' (SEQ ID NO: 28). To create mutations the PCR was done according to manufacturer's instructions using pYES2-Δ9 desaturase clones of P. ostreatus and S. cerevisiae as template DNAs. Mutational changes were confirmed by sequencing.

Lipid Analysis

Yeast cells were grown in liquid YPD medium lacking supplemental unsaturated fatty acids for 1-2 days, and total fatty acids were extracted from pellets composed of 1-2 ml of culture. The lipids were extracted into chloroform as previously described (16). The lipids were methylated with 0.5 ml of sodium methoxide (4.2%, w/v) with shaking at 800 rpm for 45 min. One milliliter of hexane was used to extract the Fatty Acid Methyl Esters (FAMES), and this was repeated once. The hexane extracts were combined and then washed with 1 ml of 0.9% KCl. The FAMES in hexane was brought down to 0.5 ml and analyzed by GC.

Soybean Transformation

Immature soybean pods with seeds of approximately 3-5 mm length were picked from cultivar Jack and the pods were sterilized by first soaking the pods in a beaker with 10% Liquinox for 1.5 minutes, followed by soaking of the pods in 70% Isopropanol for 1.5 minutes, in Liquinox plus bleach for 11 min, and then soaking the pods in sterile water twice for 5 min each. The seeds were then dissected to obtain the cotyledon without the embryonic axis and to separate the two cotyledons for each seed. The cotyledons were then placed on D40 plates and divided into 16 pieces with the flat side up. The D40 plates were covered with para film and then cultured upside down in culture room under low light conditions for 1 month. Following the initial culturing, the induced embryos were then transferred to $D_2O$ plates for proliferation.

To proliferate the embryos in liquid medium, the globular stage embryogenic cultures were transferred from $D_2O$ plates into FN liquid medium in a 125 ml flask containing 10 mg/L 2, 4-D and 3% sucrose and then placed on a shaker. The cultures were then subcultured every 7 days with fresh FN liquid medium. Embryos that had been cultured in FN liquid medium for at least one month were used for shooting. For subsequent bombardment with gold/DNA particles, small embryo clumps were placed in the center of the D20 media, on which they were to be shot with the particles, 1 day prior to the actual bombardment. Prior to bombardment, the lids were removed from the petri plates and the embryos allowed to air-dry for approximately 30 minutes in a laminar flow hood.

Soybean embryogenic suspension cultures were transformed with the plasmids and DNA fragments of interest (i.e., P. ostreatus and yeast Δ9 desaturase genes and fragments) by particle gun bombardment. A BIOLISTIC® PDS1000/He instrument (DuPont, helium retrofit) was used for all transformations. Tissue was bombarded with membrane rupture pressure set at 1100 PSI and the chamber evacuated to a vacuum of 25-27 inches of mercury. Tissue was placed approximately 3.5 inches from the retaining/stopping screen. Briefly, the procedure for preparing the DNA/gold conjugates for the particle bombardment included sterilizing each gold particle followed by the addition of approximately 500 ng of the particular DNA of interest in combination with 220 µl sterile $H_2O$, 250 µl of 2.5 M calcium chloride, and 100 µl of 0.1 M spermadine. This mixture was kept and then precipitated with 100% ethanol followed by resuspension of the mixture in appropriate volume depending on the desired concentration of DNA to be used in the bombardment procedures.

Following bombardment of the cultures, the material including the transformed tissue was left on the plate upon which they were shot for 1 day. The tissue was then placed in a 125-ml flask containing approximately 35 ml of FN lite medium (5 mg/L 2, 4-D and 1% sucrose) containing 30 mg/L hygromycin and the flasks were placed on a shaker. Transformed embryos were then selected using 30 mg/L hygromycin. At four to five weeks post selection, the green, transformed tissue was observed growing from untransformed, necrotic embryogenic clusters. Isolated, green tissue was then removed and inoculated into multi-well plates containing FN lite medium to generate new, clonally propagated, transformed embryogenic suspension cultures.

For embryo maturation, a cluster of globular-stage embryos were taken from the multi-well plate that were approximately 3 mm in diameter. These embryos were then broken apart and placed in a 125 ml flask with approximately 35 ml of liquid shoot histodifferentiation and maturation medium (SHaM). After 3 weeks, the resulting cotyledonary-stage embryos were then ready for desiccation. During this period, some individual embryos were removed and screened for alterations in their fatty acid compositions.

Matured individual embryos were desiccated by placing them into an empty petri plate for approximately 4-7 days. The plates were then sealed with para film to create a small humidity chamber. To prevent the embryos from drying out too quickly, a 1 cm piece of solidified medium was added to the plate.

To germinate the embryos, desiccated embryos were placed on ½ strength MS solid medium for a week for root formation. After root formation, the embryos were then transferred onto a filter paper bridge in wider test tubes containing the ½ strength MS liquid medium for faster shoot growth. Once the shoots reached a proper height in test tubes, they were then transferred to the Magenta boxes where a 23 hour photoperiod was used to prevent the premature induction of flowering. Once the seedlings reached a proper height, the photoperiod was then reduced to permit flowering and seed set, and subsequent transferring into soil in a greenhouse. The mature seeds were then harvested, chipped and analyzed for fatty acids and DNA from the same chip.

*Arabidopsis* Transformation

Transformations of *Arabidopsis thaliana* were performed by the floral dip method (Clough SJ and Bent AF 1998). Briefly, *Arabidopsis* ecotype Columbia plants were grown to flowering stage in a greenhouse in moistened potting soil. To obtain more floral buds per plant, inflorescences were clipped after most plants had formed primary bolts, relieving apical dominance and encouraging synchronized emergence of multiple secondary bolts. Plants were infiltrated or dipped when most, secondary inflorescences were approximately 1-10 cm tall (7 days after clipping). The plant transformation vector pCAMBIA 1301 containing a *P. ostreatus* Δ9 desaturase gene (cloned under seed-specific and 35S promoters) was then transformed into *Agrobacterium tumefaciens* GV 3850 using the freeze/thaw method described by An, et al. (1988).

For floral dip, the inoculum was added to a beaker and the plants were inverted into this suspension such that all above-ground tissues were submerged. After 5 sec of gentle agitation, then plants were then removed. The plants were subsequently left in a low light or dark location overnight and returned to the greenhouse the next day with care taken to keep domed plants out of direct sunlight. Domes were removed approximately 12-24 h after treatment. Plants were grown for a further 6 weeks until siliques were brown and dry. Seeds were harvested by gentle pulling of grouped inflorescences through fingers over a piece of clean paper. The majority of the debris was removed from the paper by gentle blowing and seeds were stored in microfuge tubes and kept at 4° C. under desiccation.

*Agrobacterium*—Mediated Tobacco Transformation

The plant transformation vector pCAMBIA 1301 containing a *P. ostreatus* Δ9 desaturase gene (cloned under seed-specific and 35S promoters) was transformed into *Agrobacterium tumefaciens* GV 3850 using the freeze/thaw method described by An, et al. (1988). The Agrobacterium were grown with the binary vector in 10 ml of YEP+100 mg/L Rifampicin+50 mg/L kanamycin O/N at 28° C. The presence of the plasmid was confirmed by performing a miniprep (2-3 ml). The remainder of culture was then centifuged at 4000 rpm for 10 min at 15° C. and the pellet was resuspended in 10 ml of YEP.

Young leaves from one month old sterile tobacco plantlets were then excised with a sterile forcep. The leaves were dropped into the *Agrobacterium* solution and cut into 2-3 pieces vertically to obtain a large leaf surface area. The leaves were incubated for 5-10 min in the solution and then blotted onto autoclaved filter paper. The leaves were then co-cultivated on TOM (-Ab) media for 4 days in the dark. The leaf segments were then transferred to TOM media containing 500 mg/L cefotaxime and 15 mg/L hygromycin and sub-cultured every two weeks. Calli and shoots appeared in 3-5 weeks and the shoots were cut and transferred onto T-media containing 500 mg/L cefotaxime and 15 mg/L hygromycin. The shoots which rooted were then transferred into pots containing pro-mix.

Petunia Transformation

Petunia plants were obtained from commercial stores. The plants were rinsed in tap water to remove any adhering debris and plants were briefly submerged into water to promote hydration of the leaf, as fully turgid leaves were preferable for infiltration. The plant transformation vector pBI 121 containing a *Pleurotus ostreatus* Δ9 desaturase gene (cloned under 35S promoter) was transformed into *Agrobacterium tumefaciens* GV 3850 by electroporation and maintained under kanamycin and rifampicin selection. Overnight cultures for infiltration were concentrated by centrifugation, resuspended in a 10% sucrose solution to a final concentration of $OD_{600}$ equal to 0.5. Petunia leaves were then nicked on the lower leaf surface, and the bacterial suspension introduced using a needle-less syringe. Infiltrated plants were maintained for up to 1 week.

Example 1

Identification of *P. ostreatus* Δ9 Desaturase

PCR with degenerate primers yielded a 550 bp fragment, which was then cloned and sequenced. An NCBI blast search indicated that the amplified product was a Δ9 desaturase, with Blast X showing that the amplified product had 80% and 59% identity with the Lentinula edodes and Cryptococcus curvatus Δ9 desaturases. Southern blot hybridization of oyster genomic DNA was then performed with the 550 bp PCR product as a probe. Depending on the restriction enzyme used 1-4 strong bands of variable sizes (3 kbp to 12 kbp or more) were visible in the Southern blot (FIG. 1) indicating the presence of more than one independent Δ9 desaturase gene or more than one copy of the Δ9 desaturase in P. ostreatus. Multiple Δ9 desaturase genes have also been reported from different organisms including higher fungi such as Mortierella sp. (4), C. elegans (3), rats (17), mice (18,19) and plants (20).

Two of the three restriction enzymes that yielded 3-5 kbp size bands in Southern blot hybridization were used to digest the genomic DNA to perform inverse-PCR to amplify the full length P. ostreatus Δ9 desaturase. However, when inverse-PCR was done different sized products were amplified with the largest being 1.6 kbp with the EcoRI digested DNA as a template. Blast analysis identified a 1.0 kbp region containing homology to known Δ9 desaturases. PCR and RT-PCR were done based on the primers designed from the sequence obtained by inverse-PCR to amplify the 1.551 kbp genomic (SEQ ID NO: 1) and approximately 1.293 kbp long cDNA (SEQ ID NO: 2) of P. ostreatus Δ9 desaturase (FIGS. 9A and 9B).

Example 2

NCBI Blast Analysis

NCBI Blast searching with the sequence from the genomic DNA clone and cDNA clone identified an N-terminal fatty acid desaturase domain (SEQ ID NO: 4) and a C-terminal cytochrome b5 domain (FIG. 2) that is common to all known fungal Δ9 desaturases (23).

Primary sequence analysis of membrane desaturases from a wide range of organisms, including mammals, fungi, cyanobacteria, insects, and plants revealed that these organisms are reported to contain three conserved regions of histidine-box motifs (24). Similar to the Δ9 desaturases from the above mentioned organisms, analysis of the P. ostreatus protein (FIG. 10) showed that the protein also contained 8 histidines in 3 cluster motifs, namely HRLWSH (SEQ ID NO: 29), HRSHH (SEQ ID NO: 30), and HNFHH (SEQ ID NO: 31).

Figure 3:
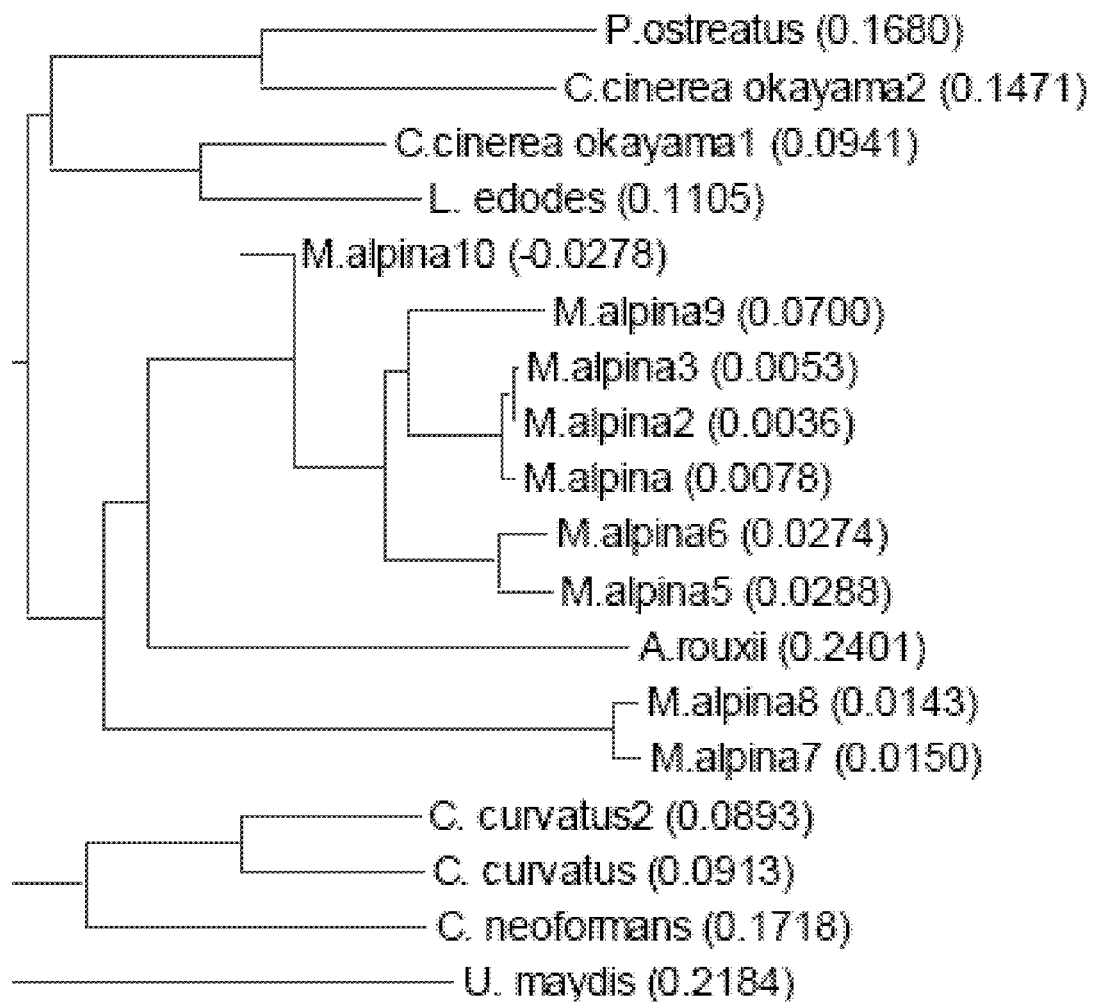
FIG. 3 is schematic diagram of a distance tree showing the homology of a *P. ostreatus* Δ9 desaturase polypeptide with other fungal desaturase polypeptides.

The P. ostreatus Δ9 desaturase amino acid sequence (SEQ ID NO: 3) showed high homology to other known fungal desaturases. A distance tree of Blast P results revealed that the hypothetical protein CG1G_11588 (Coprinopsis) had the highest homology to the P. ostreatus Δ9 desaturase with 58% identity and 75% similarity (GENBANK® Accession No. EAU81345) (FIG. 3). The homology of the P. ostreatus Δ9 desaturase to other species is further described in the following Table 1.

TABLE 1

Homology of the P. ostreatus Δ9 desaturase to other species at the amino acid level.

| | Pleurotus ostreatus | Rattus | Homo sapiens | Pichia angusta | S. cerevisiae | Mortierella alpina | Cryptococcus curvatus | Lentinula edodes |
|---|---|---|---|---|---|---|---|---|
| Pleurotus ostreatus | 100 | 72 | 33 | 47 | 36 | 51 | 49 | 53 |
| Rattus norvegicus | | 100 | 25 | 42 | 30 | 46 | 50 | 60 |
| Homo sapiens | | | 100 | 30 | 23 | 30 | 25 | 28 |
| Pichia angusta | | | | 100 | 54 | 50 | 44 | 51 |
| S. cerevisiae | | | | | 100 | 38 | 36 | 36 |
| Mortierella alpina | | | | | | 100 | 50 | 55 |
| Cryptococcus curvatus | | | | | | | 100 | 61 |
| Lentinula edodes | | | | | | | | 100 |

Example 3

Functional Analysis of the P. ostreatus Δ9 Desaturase Gene

Figure 4:
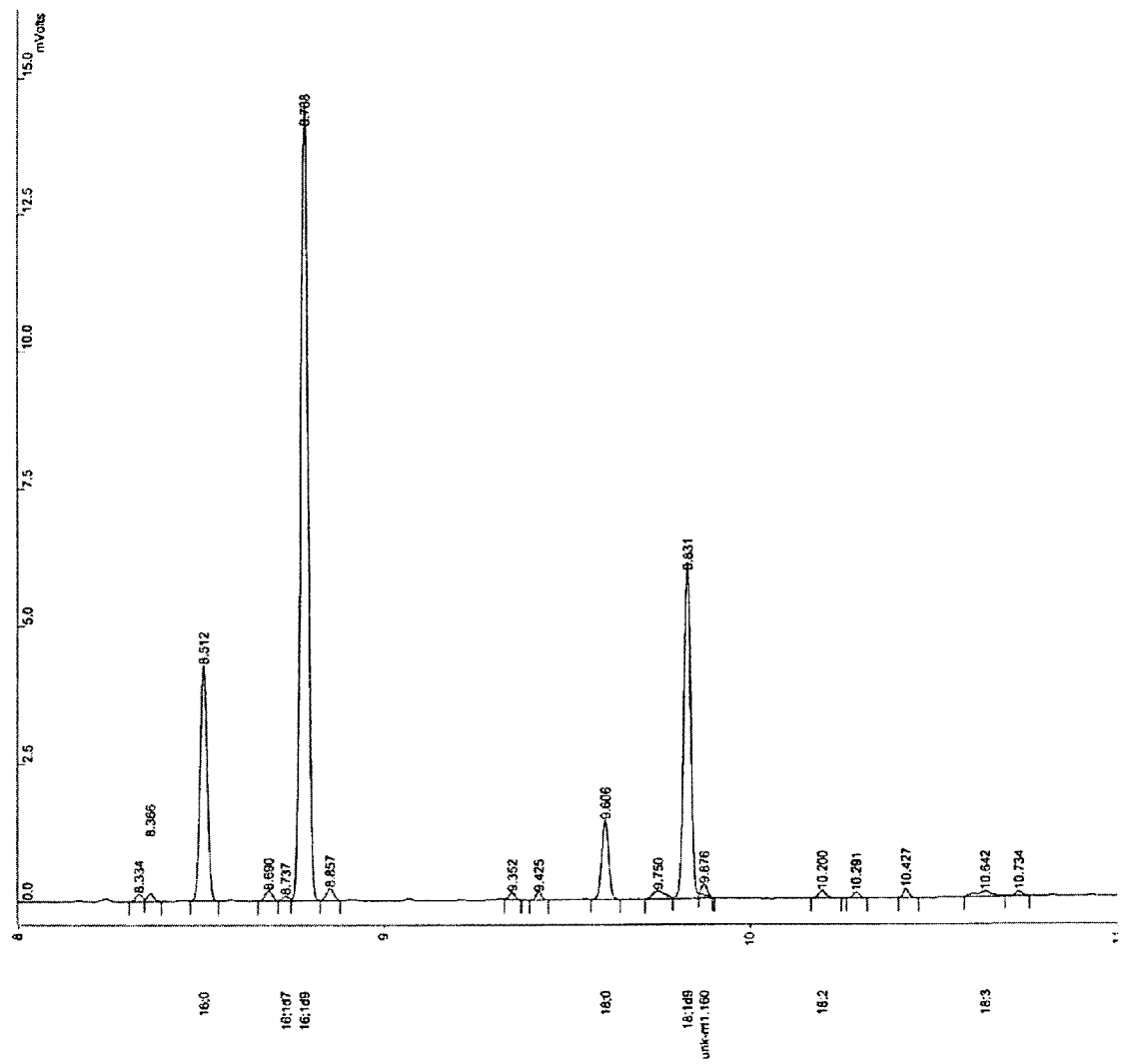
FIG. 4 is a chromatogram showing the results of a lipid analysis of a *S. cerevisiae* Δ9 desaturase mutant transformed with a *P. ostreatus* Δ9 desaturase gene.

Gas chromatography analysis of the P. ostreatus fatty acids shows linoleic acid at 58% to be the major fatty acid followed by palmitic acid at ~20% (Table 1). Similar lipid composition patterns have been reported for other Pleurotus sp. (25). The lipid composition of S. cerevisiae Δ9 desaturase mutant rescued with the P. ostreatus Δ9 desaturase and S. cerevisiae A9 desaturase genes showed palmitoleic acid to be most abundant (FIG. 4; Table 2). Palmitoyl-CoA can be slightly preferred by the yeast Δ9 desaturase as a substrate compared to the P. ostreatus desaturase as indicated by the slight increase in the percent composition of palmitoleic acid in the total lipids of the rescued mutant. The oleic acid levels in the rescued mutant indicate that the P. ostreatus desaturase has higher activity with stearoyl-CoA than the yeast desaturase (Table 2).

TABLE 2

Fatty acid composition of wild type P. ostreatus, S. cerevisiae and a yeast unsaturated fatty acid auxotroph rescued with P. ostreatus and S. cerevisiae Δ9 desaturases. Values are means of three independent experiments ± standard errors.

| Fatty acid | Content of fatty acids (%) in P. ostreatus fruiting bodies | Content of fatty acids (%) in S. cerevisiae (In VSc-1) | Content of fatty acids (%) in yeast auxotroph rescued with wild type P. ostreatus ole1 | Content of fatty acids (%) in yeast auxotroph rescued with wild type S. cerevisiae ole1 |
|---|---|---|---|---|
| 16:0 | 19.6 | 15.4 ± 0.2 | 13.7 ± 0.3 | 13.6 ± 0.1 |
| 16:1Δ7 | 0.3 | — | — | 0.2 ± 0.01 |
| 16:1Δ9 | 0.1 | 19.4 ± 0.3 | 43.0 ± 0.06 | 47.0 ± 0.2 |
| 16:2 | 0.2 | — | — | — |
| 17:0 | 0.5 | — | — | — |
| 18:0 | 1.2 | 6.2 ± 0.14 | 7.0 ± 0.11 | 4.3 ± 0.10 |
| 18:1Δ9 | 3.7 | 7.3 ± 0.3 | 27.1 ± 0.9 | 19.5 ± 0.09 |
| 19:0 | 0.1 | — | — | — |
| 18:2 | 58.1 | — | 0.6 ± 0.03 | 0.5 ± 0.01 |
| 18:3 | 0.1 | — | — | 0.7 ± 0.01 |

These results when coupled to the P. ostreatus lipid composition (Table 2) indicate that there are more than one Δ9 desaturase present in the oyster mushroom genome. The lipid composition of P. ostreatus indicated that 18:2 and 16:0 are the major fatty acids (Table 2). The levels of 16:1 compared to these two fatty acids are negligible. The Southern blot hybridization data also showed that P. ostreatus has 2-3 Δ9 desaturases (FIG. 1). Other Δ9 desaturase genes in P. ostreatus can contribute to the synthesis of the 18:1 precursor of 18:2. This is supported by the data available from the other known mushroom L. edodes Δ9 desaturase. Δ9 desaturase mutant yeast complementation with the L. edodes Δ9 desaturase showed much less 16:0 compared to 18:0 desaturation products. Similarly other known fungal Δ9 desaturases also show highest activities with 18:0 substrates (4,9). Without wishing to be bound be any particular theory, it is likely that Δ9 desaturase(s) with specificity for 18:0 substrates can be the major contributors to the P. ostreatus lipid composition. Alternatively P. ostreatus can also have higher fatty acid elongation activity from 16:0 to 18:0 than S. cerevisiae.

Example 4

Specificity of the Modified Co-A Desaturases

Even though the Δ9-stearoyl (18:0)-ACP (Acyl-acyl carrier protein) desaturases are mainly responsible for the synthesis of monounsaturated fatty acids in plants (26), several variant enzymes with different substrate specificities are also known (27-29). Some of the recent additions to this category include desaturases resembling cyanobacterial acyl lipid and mammalian and yeast Co-A desaturases (20,30) from Arabidopsis and other plants (31). Using saturation mutagenesis (32) several mutations in castor Δ9-stearoyl ACP desaturase that enhance activity with 16:0 substrates were identified. The replacement of the glycine by a leucine at residue 188 results in an enzyme that is 10-fold more active with 14:0-ACP and 15-fold more active with 16:0-ACP than the wild-type castor enzyme (32), presumably due to a modification of the substrate binding pocket size such that smaller fatty acid molecules are accommodated in place of larger fatty acids such as 18:0. This mutant was also more than 50-fold less active with 18:0-ACP relative to the wild-type Δ9-ACP desaturase enzyme. However, no similar studies were reported that dealt with the structure functional aspect of acyl-lipid or Co-A desaturases. Although, previous reports showed that by switching the subcellular targeting of Arabidopsis desaturases ADS3, ADS1 and ADS2, their regiospecificities were changed (33).

Although there are minimal structural similarities between ACP & Co-A desaturases, alignment of similar portions of different ACP and Co-A desaturases from Ricinus communis, Asclepias syriaca, Brassica juncea, Brassica napus, Carthamus tinctorius, Cucumis sativus, Arachis hypogaea, Elaeis guineensis, Thunbergia alata, Homo sapiens, Rattus norvegicus, Caenorhabditis elegans a, Caenorhabditis elegans b, Caenorhabditis elegans c, Saccharomyces cerevisiae, Pichia angusta, Cryptococcus curvatus, Amylomyces rouxii, and P. ostreatus (SEQ ID NOS: 32-50, respectively) shows that the glycine residue involved in substrate specificity in ACP-desaturases is conserved in Co-A desaturases also (FIG. 5). In vitro mutagenesis was performed to convert the corresponding glycine residue (G245) in P. ostreatus Δ9 Co-A desaturase to leucine. A similar mutation was done in the Δ9 desaturase of S. cerevisiae. The function of the mutated desaturases was examined by transforming the S. cerevisiae Δ9 desaturase mutant. The amount of palmitic acid in total lipids of the transformed Δ9 desaturase mutant is 52% with the mutated P. ostreatus enzyme and 39% with the modified S. cerevisiae enzyme (Table 3). Similarly the 16:1 levels were only 8% and 0.5% of total lipids with the mutant P. ostreatus and S. cerevisiae enzymes (Table 3). These results indicate that the glycine residue that appeared conserved among Δ9 CoA desaturases is important for activity but not for substrate specificity in CoA desaturases unlike ACP desaturases (32). Based on hydropathy analyses of the sequences of rat and yeast stearoyl-CoA desaturase (15), previous reports have proposed a structural model of membrane bound Δ9 desaturases consisting of four membrane-spanning domains with the N and C termini as well as the catalytic site being oriented toward the cytosolic side of the membrane with conserved His residues serving as ligands for the iron cofactor of these enzymes (34). Through mutagenesis others have shown that all conserved histidine residues are catalytically important in Rat-Co-A desaturase (35). However, in the presently-described experiments replacement of the conserved glycine 245 residue with leucine made both the P. ostreatus and S. cerevisiae Δ9 Co-A desaturases nearly dysfunctional as the mutant enzyme still has sufficient functionality to rescue the S. cerevisiae auxotroph. This indicates that this glycine (245) plays a major role in the activity of this protein by maintaining secondary structure of these proteins or by playing a role at the active site of the proteins.

TABLE 3

Fatty acid composition of a yeast auxotroph rescued with G188L mutant forms of P. ostreatus, S. cerevisiae 9 desaturases. Values are mean of three independent experiments ± standard errors.

| Fatty acid | Content of fatty acids (%) in yeast auxotroph rescued with mutated form of P. ostreams ole1 | Content of fatty acids (%) in yeast auxotroph rescued with mutated form of S. cerevisiae ole1 |
|---|---|---|
| 16:0 | 52.0 ± 0.8 | 39.0 ± 0.8 |
| 16:1Δ7 | — | 0.1 ± 0.02 |
| 16:1Δ9 | 8.0 ± 0.2 | 0.5 ± 0.03 |
| 16:2 | — | — |
| 17:0 | — | 0.1 ± 0.03 |
| 18:0 | 3.2 ± 0.09 | 1.4 ± 0.09 |
| 18:1Δ9 | 2.5 ± 0.2 | 3.3 ± 0.1 |
| 19:0 | — | — |
| 18:2 | — | — |
| 18:3 | — | — |

In the auxotroph rescue studies described herein above, the rescue time for the yeast Δ9 desaturase mutant with mutated Co-A desaturases of P. ostreatus and S. cerevisiae took 3 weeks compared to the wild type genes which took only one week on yeast minimal media plates. Others also report that the L. edodes and S. cerevisiae genes took a week to rescue a yeast unsaturated fatty acid auxotroph (11).

Example 5

Analysis of Monounsaturated Fatty Acids in Transgenic Plant Lines

Figure 6:
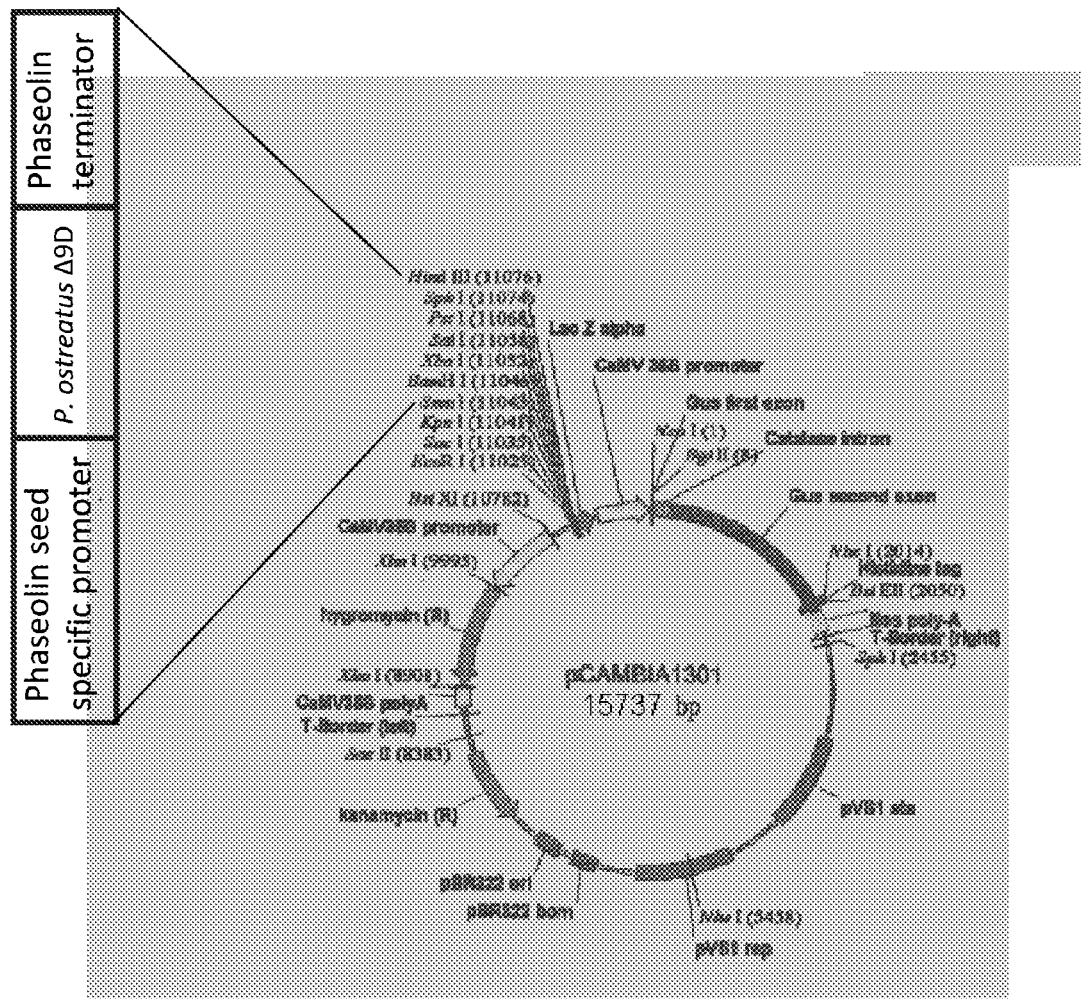
FIG. 6 is a schematic diagram depicting the cloning of a *P. ostreatus* Δ9 desaturase gene under the control of a phaseolin seed-specific promoter into a pCAMBIA 1301 plant transformation vector.

Several transgenic lines of Glycine max (soybean), Nicotiana tabacum (tobacco), and Arabidopsis thaliana (Arabidopsis) were transformed with a pCAMBIA 1301 expression vector containing a P. ostreatus or yeast Δ9 desaturase nucleic acid under the control of a seed-specific phaseolin promoter or a 35S promoter, or were transformed with linearized DNA fragments of a P. ostreatus or yeast Δ9 desaturase nucleic acid sequence. The P. ostreatus and yeast Δ9 desaturase genes cloned under seed-specific promoters (see, e.g. FIG. 6) were introduced into soybean somatic embryos through the particle bombardment method described herein in the Examples, while the same genes were introduced into tobacco and Arabidopsis through Agrobacterium transformation as also described herein. Gas chromatography analysis showed considerable increases in palmitoleic acid (16:1) and oleic acid (18:1) in all three transgenic lines versus the vector control (Tables 4 (soybean), 5 (tobacco), and 6 (Arabidopsis)), with matured soybean transgenic embryos showing a 40 to 45 fold increase in palmitoleic acid (16:1) over the vector control.

TABLE 4

Several soybean (*G. max*) transgenic lines with the introduced *P. ostreatus* and yeast Δ9 desaturase (D9D) genes were analyzed for the 16:1 content by GC at the matured somatic embryo level and at the seed by using a seed-specific promoter. The leaves were analyzed by using a constitutive promoter. (SSP—Seed-specific Promoter; WP—Whole plasmid; LDF—Linearized DNA fragment).

| | SSP (WP) | | | | SSP (LDF) | | | | 35S | |
| --- | --- | --- | --- | --- | --- | --- | --- | --- | --- | --- |
| | SE | | Seeds | | SE | | Seeds | | Leaves | |
| Gene construct | 16:1 (%) | 18:1 (%) | 16:1 (%) | 18:1 (%) | 16:1 (%) | 18:1 (%) | 16:1 (%) | 18:1 (%) | 16:1 (%) | 18:1 (%) |
| Vector control | 0.02 | 1.48 | 0.01 | 14.5 | 0.02 | 2.41 | 0.13 | 16.0 | 0.02 | 1.71 |
| *P. ostreatus* D9D | 0.81 | 3.70 | 0.76 | 43.0 | 0.82 | 3.86 | 1.2 | 41.0 | 0.86 | 2.81 |
| yeast D9D | 0.94 | 3.84 | 0.92 | 45.0 | 0.89 | 3.21 | 1.67 | 49.0 | 1.45 | 3.86 |

TABLE 5

Tobacco (*N. tabacum*) transgenic lines with the introduced *P. ostreatus* and yeast Δ9 desaturase (D9D) genes cloned under seed-specific and constitutive promoters were analyzed. Analysis of different plant tissue of the *N. tabacum* shows differences in fatty acyl composition due to the expression of the *P. ostreatus* and yeast genes. (SSP—Seed-specific Promoter; WP—Whole plasmid; LDF—Linearized DNA fragment).

| | 35S promoter | | | | | | | | SSP | |
| --- | --- | --- | --- | --- | --- | --- | --- | --- | --- | --- |
| | Leaves | | Stems | | Roots | | Seeds | | Seeds | |
| Gene construct | 16:1 (%) | 18:1 (%) | 16:1 (%) | 18:1 (%) | 16:1 (%) | 18:1 (%) | 16:1 (%) | 18:1 (%) | 16:1 (%) | 18:1 (%) |
| Vector control | 0.07 | 3.3 | 0.17 | 3.9 | 0.11 | 1.9 | 0.12 | 9.6 | 0.04 | 7.1 |
| *P. ostreatus* D9D | 0.39 | 2.4 | 2.0 | 2.1 | 1.2 | 2.6 | 0.26 | 6.1 | 0.16 | 4.2 |
| Yeast D9D | 4.7 | 5.0 | 7.3 | 6.4 | 6.9 | 11.2 | 1.1 | 7.2 | 0.45 | 9.8 |

TABLE 6

*Arabidopsis* transgenic lines with the introduced *P. ostreatus* and yeast Δ9 desaturase (D9D) genes cloned under seed-specific and constitutive promoter were analyzed. The T2 seed was germinated on the selection media and the transformants were selected and transplanted into soil. The lipids were extracted from the leaves and seed material were analyzed by GC. (SSP—Seed-specific Promoter; WP—Whole plasmid; LDF—Linearized DNA fragment).

| | 35S promoter | | | | SSP | |
| --- | --- | --- | --- | --- | --- | --- |
| | Leaves | | Seeds | | Seeds | |
| Gene construct | 16:1 (%) | 18:1 (%) | 16:1 (%) | 18:1 (%) | 16:1 (%) | 18:1 (%) |
| Vector control | 0.26 | 4.1 | 0.11 | 7.2 | 0.04 | 6.8 |
| *P. ostreatus* D9D | 1.23 | 3.2 | 0.49 | 5.7 | 0.52 | 2.9 |
| yeast D9D | 2.41 | 5.6 | 1.3 | 6.8 | 0.85 | 9.3 |

Petunia plants transformed with transformation vector pBI 121 containing a *Pleurotus ostreatus* Δ9 desaturase gene by the agroinfiltration methods described herein above also showed an increased percentage of palmitoleic acid (16:1) and oleic acid (18:1) as compared to the vector controls. Gas chromatography analysis of various transgenic petunia leaves introduced with a *P. ostreatus* Δ9 desaturase genomic DNA clone showed the percentage of palmitoleic acid (16:1) to be as high as 22.5% while levels of oleic acid (18:1) were as high as 9.8% (Table 7).

TABLE 7

Gas chromatography data from petunia transgenic leaves (1-6) and a vector control (VC). The amount of each fatty acid detected is expressed a percentage of the total amount of fatty acids detected.

| | VC | 1 | 2 | 3 | 4 | 5 | 6 |
| --- | --- | --- | --- | --- | --- | --- | --- |
| 14:0me (%) | 1.0 | 1.1 | 0.5 | 0.8 | 0.5 | 0.1 | 0.1 |
| 16:0me (%) | 14.1 | 21.9 | 16.1 | 25.6 | 17.6 | 20.5 | 21.2 |

TABLE 7-continued

Gas chromatography data from petunia transgenic leaves (1-6) and a vector control (VC). The amount of each fatty acid detected is expressed a percentage of the total amount of fatty acids detected.

|  | VC | 1 | 2 | 3 | 4 | 5 | 6 |
|---|---|---|---|---|---|---|---|
| 16:1d7me | 0.8 | 0.9 | 0.9 | 0.3 | 1.4 | 0.0 | 0.0 |
| 16:1d9me | 0.0 | 6.3 | 1.3 | 1.1 | 2.2 | 22.5 | 22.5 |
| 18:0+16:3me | 2.5 | 7.2 | 3.1 | 5.1 | 3.6 | 10.1 | 10.5 |
| 18:1d9me | 0.5 | 2.8 | 1.6 | 1.7 | 1.9 | 5.5 | 5.7 |
| 18:1d11me | 0.0 | 3.5 | 0.8 | 1.4 | 1.2 | 9.7 | 9.8 |
| 18:2me | 9.0 | 8.2 | 10.5 | 12.1 | 11.5 | 7.6 | 7.4 |
| 18:3me | 70.9 | 46.4 | 64.0 | 49.0 | 57.9 | 23.9 | 22.7 |
| 22:0me | 1.2 | 1.6 | 1.1 | 3.0 | 2.2 | 0.0 | 0.0 |

Example 6

Expression of *P. Ostreatus* Δ9 Desaturase in Transgenic Lines

Figure 7:
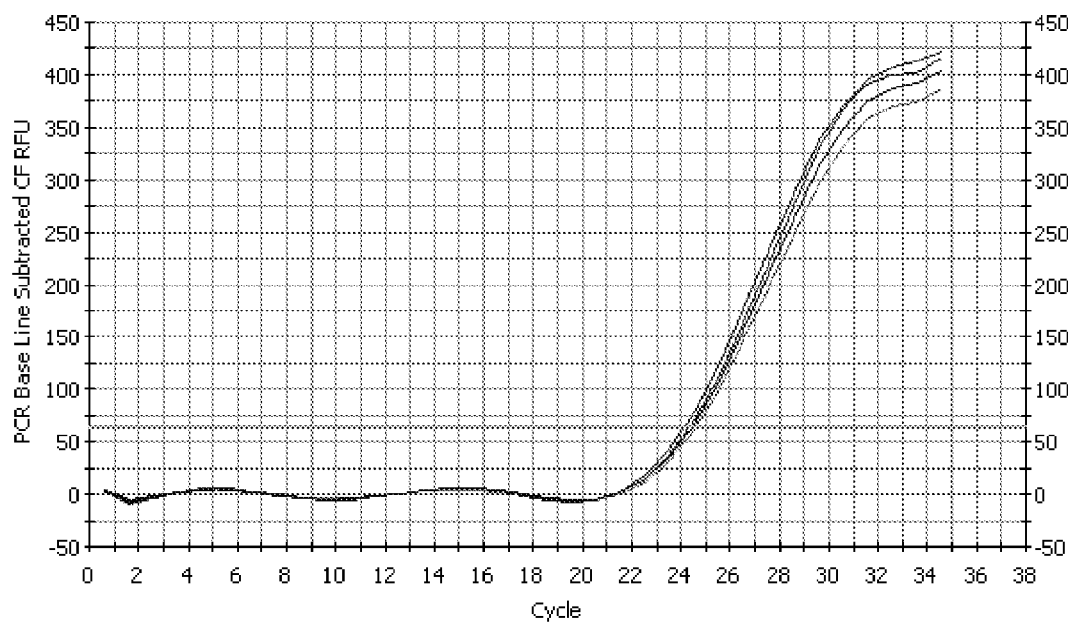
FIG. 7 is a graph showing data from quantitative real time PCR of *P. ostreatus* Δ9 desaturase mRNA levels in soybean transgenic lines where the data are expressed as relative fluorescent units (RFU) versus PCR cycle.
Figure 8:
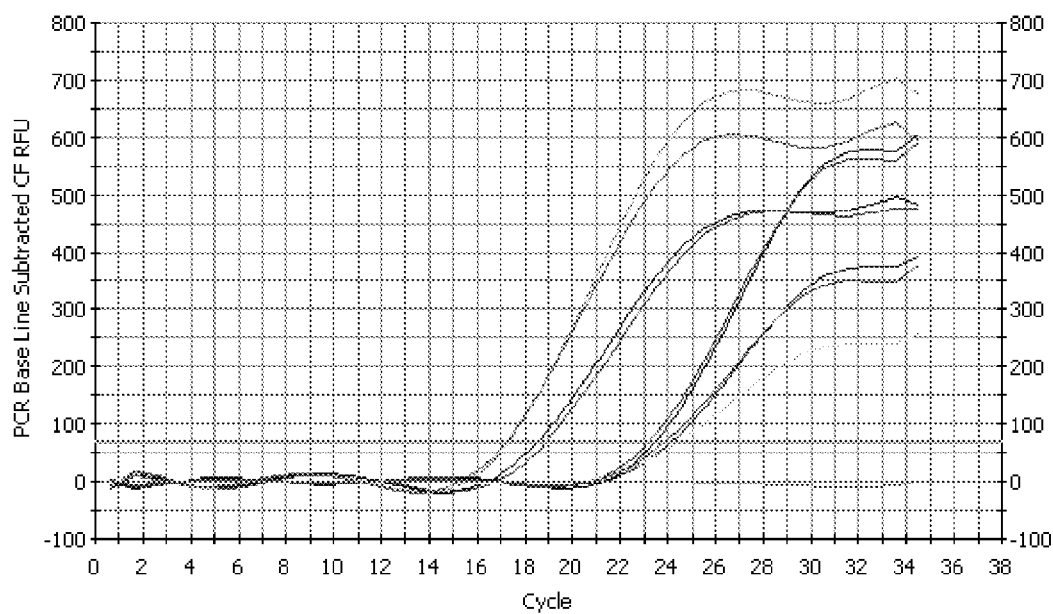
FIG. 8 is a graph showing data from quantitative real time PCR of yeast Δ9 desaturase mRNA levels in soybean transgenic lines where the data are expressed as relative fluorescent units (RFU) versus PCR cycle.

The expression levels of the *P. ostreatus* and yeast Δ9 desaturase genes in the soybean transgenic lines exhibiting the highest amounts of palmitoleic acid (16:1) were analyzed by quantitative real-time reverse transcription PCR (qRT-PCR) using SYBR Green I according to recommended protocols. Briefly, total RNA was isolated from 3 week old mature somatic embryos, cDNA created, and the qRT-PCR performed. Analysis of the qRT-PCR indicates that the *P. ostreatus* Δ9 desaturase gene (FIG. 7) and the yeast Δ9 desaturase gene (FIG. 8) are both moderately expressed in the soybean transgenic lines.

Throughout this document, various references are mentioned. All such references are incorporated herein by reference, including the references set forth in the following list:

REFERENCES

1. Mitchell, A., Martin C E. 1995. A novel cytochrome b5-like domain is linked to the carboxyl terminus of the *Saccharomyces cerevisiae* delta-9 fatty acid desaturase. *J Biol Chem.* 270: 29766-29772.
2. Petrini, G., Altabe, S G, Uttaro, A D. 2004. *Trypanosoma brucei* oleate desaturase may use a cytochrome b5-like domain in another desaturase as an electron donor. *Eur. J. Biochem.* 271: 1079-1086.
3. Watts, J., Browse, J. 2000. A Palmitoyl-CoA-Specific 9 Fatty Acid Desaturase from *Caenorhabditis elegans*. *Biophys Biochem Res Commun.* 272: 263-269.
4. Wongwathanarat, P., L. V. Michaelson, A. T. Carter, C. M. Lazarus, G. Griffiths, A. K. Stobart, D. B. Archer, and D. A. MacKenzie. 1999. Two fatty acid Delta 9-desaturase genes, ole1 and ole2, from *Mortierella alpina* complement the yeast ole1 mutation. *Microbiology*-(UK) 145: 2939-2946.
5. Prasad, M., Joshi V C 1979. Purification and properties of hen liver microsomal terminal enzyme involved in stearoyl coenzyme A desaturation and its quantitation in neonatal chicks. *J Biol Chem.* 254: 6362-6368.
6. Strittmatter, P., Spatz L, Corcoran D, Rogers M J, Setlow B, Redline R. 1974. Purification and properties of rat liver microsomal stearyl coenzyme A desaturase. *Proc Natl Acad Sci.* 71: 4565-4569.
7. Choi J Y, S. J., Hwang S Y, Martin C E. 1996. Regulatory elements that control transcription activation and unsaturated fatty acid-mediated repression of the *Saccharomyces cerevisiae* OLE1 gene. J Biol Chem. 271: 3581-3589.
8. Gonzalez, C., Martin C E. 1996. Fatty acid-responsive control of mRNA stability. Unsaturated fatty acid-induced degradation of the *Saccharomyces* OLE1 transcript. *J Biol Chem.* 271: 25801-25809.
9. Anamnart, S., Tomita T, Fukui F, Fujimori K, Harashima S, Yamada Y, Oshima Y. 1997. The P-OLE1 gene of *Pichia angusta* encodes a delta 9-fatty acid desaturase and complements the ole1 mutation of *Saccharomyces cerevisiae*. *Gene.* 184: 299-306.
10. Kajiwara, S. 2002. Molecular cloning and characterization of the Delta9 fatty acid desaturase gene and its promoter region from *Saccharomyces kluyveri*. *FEMS Yeast Res* 2: 333-339.
11. Sakai, H., Kajiwara, S. 2003 A stearoyl-CoA-specific Delta 9 fatty acid desaturase from the basidiomycete *Lentinula edodes*. *Biosci Biotechnol Biochem.* 67: 2431-2437.
12. Reddy, M. S. S., R. D. Dinkins, C. T. Redmond, S. A. Ghabrial, and G. B. Collins. 2001. Expression of Bean pod mottle virus (BPMV) coat protein precursor results in resistance to (BPMV) in transgenic soybeans. *Phytopathology.* 91: 831-838.
13. Sambrook, J., Russell, D W. 2001. Molecular Cloning: A Laboratory Manual.
14. Gietz, R. D., R. H. Schiestl, A. R. Willems, R. A. Woods, and K. S. 1995. Studies on the Transformation of Intact Yeast Cells by the LiAc/SS-DNA/PEG Procedure. Yeast. 11: 355-360.
15. Stukey, J., McDonough, V M, Martin, C E. 1990. The OLE1 gene of *Saccharomyces cerevisiae* encodes the delta 9 fatty acid desaturase and can be functionally replaced by the rat stearoyl-CoA desaturase gene. *J. Biol. Chem.* 265: 20144-20149
16. Bligh, E. G., and W. J. Dyer. 1959 A Rapid Method of Total Lipid Extraction and Purification. *Can. J. Biochem. Physiol.* 37: 911-917.
17. Mihara, K. 1990. Structure and Regulation of Rat Liver Microsomal Stearoyl-CoA Desaturase Gene. *J. Biochem.* (Tokyo) 108: 1022-1029.
18. Kaestner, K. H., Ntambi, J. M., Kelly, T. J., Jr., and Lane, M. D. 1989. Differentiation-induced gene expression in 3T3-L1 preadipocytes. A second differentially expressed gene encoding stearoyl-CoA desaturase. *J. Biol. Chem.* 264: 14755-11476.
19. Miyazaki, M., Jacobson, M. J., Man, W. C., Cohen, P., Asilmaz, E., Friedman, J. M., and Ntambi, J. M. 2003. Identification and characterization of murine SCD4, a novel heart-specific stearoyl-CoA desaturase isoform regulated by leptin and dietary factors. *J. Biol. Chem.* 278: 33904-33911
20. Fukuchi-Mizutani, M., Tasaka, Y., Tanaka, Y., Ashikari, T., Kusumi, T. and Murata, N. 1998. Characterization of 9 acyl-lipid desaturase homologues from *Arabidopsis thaliana*. *Plant Cell Physiol.* 39: 247-253.
21. Hui, E., Wang P C and Lo S J. 1998. Strategies for cloning unknown cellular flanking DNA sequences from foreign integrants. *Cell Mol Life Sci.* 54: 1403-1411.
22. Forster, C., Arthur, E, Cresp, S, Hobbs, S L, Mullineaux, P, and Casey, R. 1994. Isolation of a pea (*Pisum sativum*) seed lipoxygenase promoter by inverse polymerase chain reaction and characterization of its expression in transgenic tobacco. *Plant Mol Biol.* 26: 235-248.
23. Martin, C., Oh C S, Kandasamy P, Chellapa R, Vemula M. 2002. Yeast desaturases. *Biochem Soc Trans.* 30: 1080-1082.

24. Man, W., Miyazaki, M, Chu, K, Ntambi, J M 2006. Membrane Topology of Mouse Stearoyl-CoA Desaturase. *J. Biol. Chem.* 281: 1251-1260.
25. Dimou, D. M., Georgala, A., Komaitis, M., Aggelis, G. 2002. Mycelial fatty acid composition of *Pleurotus* spp. and its application in the intrageneric differentiation. *Mycological Research* 106: 925-929.
26. Shanklin, J., Cahoon, E. B. 1998. Desaturation And Related Modifications Of Fatty Acids. *Annu. Rev. Plant Physiol. Plant Mol. Biol.* 49: 611-641.
27. Cahoon, E. B., Shanklin, J, Ohlrogge, J. B. 1992. Expression of a coriander desaturase results in petroselinic acid production in transgenic tobacco. *Proc. Natl. Acad. Sci. USA* 89: 11184-11188.
28. Cahoon, E. B., Ohlrogge, J. B. (1994). 104, 827-844. 1994. Metabolic Evidence for the Involvement of a [delta] 4-Palmitoyl-Acyl Carrier Protein Desaturase in Petroselinic Acid Synthesis in Coriander Endosperm and Transgenic Tobacco Cells. *Plant Physiol.* 104: 827-844.
29. Schultz, D J, Cahoon, EB, Shanklin, J, Craig, R, Cox-Foster, DL, Mumma, R O, and J. I. Medford. 1996. Expression of a delta 9 14:0-acyl carrier protein fatty acid desaturase gene is necessary for the production of omega 5 anacardic acids found in pest-resistant geranium (Pelargonium xhortorum). *Proc. Natl. Acad. Sci. USA* 93: 8771-8775.
30. Mekhedov, S., O. M. de Ilarduya, and J. Ohlrogge. 2000. Toward a Functional Catalog of the Plant Genome. A Survey of Genes for Lipid Biosynthesis. *Plant Physiol.* 122: 389-402.
31. Marillia, E. F., E. M. Giblin, P. S. Covello, and D. C. Taylor. 2002. A desaturase-like protein from white spruce is a Delta (9) desaturase. *FEBS Letters* 526: 49-52.
32. Cahoon, E., Shanklin, J. 2000. Substrate-dependent mutant complementation to select fatty acid desaturase variants for metabolic engineering of plant seed oils. *Proc Natl Acad Sci USA* 97: 12350-12355.
33. Heilmann, I., S. Mekhedov, B. King, J. Browse, and J. Shanklin. 2004. Identification of the Arabidopsis Palmitoyl-Monogalactosyldiacylglycerol {Delta}7-Desaturase Gene FADS, and Effects of Plastidial Retargeting of *Arabidopsis Desaturases* on the fad5 Mutant Phenotype. *Plant Physiol.* 136: 4237-4245.
34. Fox, B. G., Shanklin, J., Somerville, C., Munck, E. 1993. Stearoyl-Acyl Carrier Protein 9Desaturase from Ricinus communis is a Diiron-Oxo Protein. *Proc. Natl. Acad. Sci. USA* 90: 2486-2490.
35. Shanklin, S., Whittle, E, Fox, BG. 1994. Eight Histidine Residues Are Catalytically Essential in a Membrane-Associated Iron Enzyme, Stearoyl-CoA Desaturase, and Are Conserved in Alkane Hydroxylase and Xylene Monooxygenase. *Biochemistry.* 33: 12787-12794.
36. An G, Ebert P R, Mitra A, Ha S B. 1988. Binary vectors. In SB Gelvin, RA Schilperoort, eds., Plant Molecular Biology Manual. Kluwer Academic Publishers, Dordrecht, pp 1-19.
37. U.S. Pat. No. 4,459,355 to Cello, et al., issued Jul. 10, 1984, and entitled "Method for transforming plant cells."
38. U.S. Pat. No. 4,536,475 to Anderson, issued Aug. 20, 1985, and entitled "Plant vector."
39. U.S. Pat. No. 4,683,195 to Mullis, et al., issued Jul. 28, 1987, and entitled "Process for amplifying, detecting, and/or-cloning nucleic acid sequences."
40. U.S. Pat. No. 4,945,050 to Sanford, et al., issued Jul. 31, 1990, and entitled "Method for transporting substances into living cells and tissues and apparatus therefore."
41. U.S. Pat. No. 5,036,006 to Sanford, et al., issued Jul. 30, 1991, and entitled "Method for transporting substances into living cells and tissues and apparatus therefore."
42. U.S. Pat. No. 5,100,792 to Sanford, et al., issued Mar. 31, 1992, and entitled "Method for transporting substances into living cells and tissues."
43. U.S. Pat. No. 5,177,010 to Goldman, et al., issued Jan. 5, 1993, and entitled "Process for transforming corn and the products thereof"
44. U.S. Pat. No. 5,179,022 to Sanford, et al., issued Jan. 12, 1993, and entitled "Biolistic apparatus for delivering substances into cells and tissues in a non-lethal manner."
45. U.S. Pat. No. 5,187,073 to Goldman, et al., issued Feb. 16, 1993, and entitled "Process for transforming gramineae and the products thereof."
46. U.S. Pat. No. 5,204,253 to Sanford, et al., issued Apr. 20, 1993, and entitled "Method and apparatus for introducing biological substances into living cells."
47. U.S. Pat. No. 5,371,014 to Matsuyama, et al., issued Dec. 6, 1994, "Process for the production of optically active 2-hydroxy acid esters using microbes to reduce the 2-oxo precursor."
48. U.S. Pat. No. 5,405,765 to Vasil, et al., issued Apr. 11, 1995, and entitled "Method for the production of transgenic wheat plants."
49. U.S. Pat. No. 5,464,763 to Schilperoort, et al., issued Nov. 7, 1995, and entitled "Process for the incorporation of foreign DNA into the genome of dicotyledonous plants."
50. U.S. Pat. No. 5,478,744 to Sanford, et al., issued Dec. 26, 1995, and entitled "Method for transporting substances into living cells and tissues and apparatus therefore."
51. U.S. Pat. No. 5,484,956 to Lundquist, et al., issued Jan. 16, 1996, and entitled "Fertile transgenic *Zea mays* plant comprising heterologous DNA encoding *Bacillus thuringiensis* endotoxin."
52. U.S. Pat. No. 5,489,520 to Adams, et al., issued Feb. 6, 1996, and entitled "Process of producing fertile transgenic *zea mays* plants and progeny comprising a gene encoding phosphinothricin acetyl transferase."
53. U.S. Pat. No. 5,508,468 to Lundquist, et al., issued Apr. 16, 1996, and entitled "Fertile transgenic corn plants."
54. U.S. Pat. No. 5,510,318 to Patel, et al., issued Apr. 23, 1996, and entitled "Herbicidal oxazine ethers."
55. U.S. Pat. No. 5,538,877 to Lundquist, et al., issued Jul. 23, 1996, and entitled "Method for preparing fertile transgenic corn plants."
56. U.S. Pat. No. 5,554,798 to Lundquist, et al., issued Sep. 10, 1996, and entitled "Fertile glyphosate-resistant transgenic corn plants."
57. U.S. Pat. No. 5,565,346 to Facciotti, issued Oct. 15, 1996, and entitled "Transformation and regeneration system for legumes."
58. European Patent No. 267,159.
59. European Patent No. 604,662.
60. European Patent No. 672,752.
61. European Patent No. 442,174.
62. European Patent No. 486,233.
63. European Patent No. 486,234.
64. European Patent No. 539,563.
65. European Patent No. 674,725.
66. International Patent Application Publication No. WO 91/02071.
67. International Patent Application Publication No. WO 95/06128.
68. Batzer et al. (1991) *Nucleic Acid Res* 19: 5081.
69. Ohtsuka et al. (1985) *J Biol Chem* 260: 2605-2608.
70. Rossolini et al. (1994) *Mol Cell Probes* 8:91-98.

71. Molecular Cloning A Laboratory Manual (1989), 2nd Ed., Sambrook, Fritsch and Maniatis, eds., Cold Spring Harbor Laboratory Press, Chapters 16 and 17.
72. DNA Cloning, Volumes I and II, Glover, ed., 1985.
73. Polynucleotide Synthesis, M. J. Gait, ed., 1984.
74. Nucleic Acid Hybridization, D. Hames & S. J. Higgins, eds., 1984.
75. Transcription and Translation, B. D. Hames & S. J. Higgins, eds., 1984.
76. Culture Of Animal Cells, R. I. Freshney, Alan R. Liss, Inc., 1987.
77. Immobilized Cells And Enzymes, IRL Press, 1986.
78. Perbal (1984), A Practical Guide To Molecular Cloning. Academic Press, Inc., N.Y.
79. Gene Transfer Vectors For Mammalian Cells, J. H. Miller and M. P. Calos, eds., Cold Spring Harbor Laboratory, 1987.
80. Methods In Enzymology, Vols. 154 and 155, Wu et al., eds., Academic Press Inc., N.Y.
81. Immunochemical Methods In Cell And Molecular Biology (Mayer and Walker, eds., Academic Press, London, 1987.
82. Handbook Of Experimental Immunology, Volumes I-IV, D. M. Weir and C. C. Blackwell, eds., 1986.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. An isolated nucleic acid comprising a sequence encoding a mushroom desaturase polypeptide, wherein the mushroom desaturase polypeptide is active with palmitic acid and stearic acid, and wherein the isolated nucleic acid sequence comprises the sequence of SEQ ID NO: 1, SEQ ID NO: 2, or a degenerate variant of SEQ ID NO: 1 or SEQ ID NO: 2.

2. The isolated nucleic acid of claim 1, wherein the nucleic acid encodes an amino acid sequence of SEQ ID NO: 3.

3. The isolated nucleic acid of claim 1, wherein the nucleic acid encodes an amino acid sequence of SEQ ID NO: 4.

4. A vector comprising the isolated nucleic acid of claim 1.

5. The vector of claim 4, wherein the isolated nucleic acid is operably linked to an expression cassette.

6. The vector of claim 5, wherein the expression cassette comprises a seed-specific promoter.

7. The vector of claim 5, wherein the expression cassette comprises a constitutive promoter.

8. An isolated polypeptide comprising a mushroom desaturase polypeptide, wherein the mushroom desaturase polypeptide is active with palmitic acid and stearic acid, and wherein the polypeptide has an amino acid sequence comprising the sequence of SEQ ID NO: 3 or SEQ ID NO: 4.

9. The polypeptide of claim 8, wherein the polypeptide is encoded by a nucleic acid sequence comprising the sequence of SEQ ID NO: 1 or a degenerate variant of SEQ ID NO: 1.

10. The polypeptide of claim 8, wherein the polypeptide is encoded by a nucleic acid sequence comprising the sequence of SEQ ID NO: 2 or a degenerate variant of SEQ ID NO: 2.

11. The polypeptide of claim 8, wherein the polypeptide is isolated from *P. ostreatus*.

12. The polypeptide of claim 8, wherein the polypeptide is a *P. ostreatus* Δ9 desaturase polypeptide.

13. A transgenic plant cell comprising a nucleic acid which comprises a sequence encoding a mushroom desaturase polypeptide, wherein the mushroom desaturase polypeptide is active with palmitic acid and stearic acid, and wherein the nucleic acid sequence comprises the sequence of SEQ ID NO: 1, SEQ ID NO: 2, or a degenerate variant of SEQ ID NO: 1 or SEQ ID NO: 2.

14. The transgenic plant cell of claim 13, wherein the plant cell is selected from the group consisting of an Arabidopsis plant cell, a tobacco plant cell, a soybean plant cell, a petunia plant cell, a canola plant cell, a rapeseed plant cell, a palm plant cell, a sunflower plant cell, a cotton plant cell, a corn plant cell, a peanut plant cell, a flax plant cell, and a sesame plant cell.

15. The transgenic plant cell of claim 13, wherein the nucleic acid encodes an amino acid sequence of SEQ ID NO: 3.

16. The transgenic plant cell of claim 13, wherein the nucleic acid encodes an amino acid sequence of SEQ ID NO: 4.

17. The transgenic plant cell of claim 13, wherein the nucleic acid is operably linked to an expression cassette.

18. The transgenic plant cell of claim 17, wherein the expression cassette comprises a seed-specific promoter.

19. The transgenic plant cell of claim 17, wherein the expression cassette comprises a constitutive promoter.

20. A method of producing a monounsaturated fatty acid, comprising:
   transforming a cell with a nucleic acid which comprises a sequence encoding a mushroom desaturase polypeptide, wherein the mushroom desaturase polypeptide is active with palmitic acid and stearic acid, and wherein the nucleic acid sequence comprises the sequence of SEQ ID NO: 1, SEQ ID NO: 2, or a degenerate variant of SEQ ID NO: 1 or SEQ ID NO: 2;
   expressing the mushroom desaturase polypeptide, wherein expression of the mushroom desaturase polypeptide increases an amount of the monounsaturated fatty acid in the cell; and
   extracting an oil containing the increased amount of the monounsaturated fatty acid from the cell.

21. The method of claim 20, wherein the nucleic acid encodes an amino acid sequence of SEQ ID NO: 3.

22. The method of claim 20, wherein the nucleic acid encodes an amino acid sequence of SEQ ID NO: 4.

23. The method of claim 20, wherein the nucleic acid is operably linked to an expression cassette.

24. The method of claim 23, wherein the expression cassette comprises a seed-specific promoter.

25. The method of claim 23, wherein the expression cassette comprises a constitutive promoter.

26. The method of claim 20, wherein the monounsaturated fatty acid is palmitoleic acid.

27. The method of claim 20, wherein the monounsaturated fatty acid is oleic acid.

* * * * *